United States Patent
Phan et al.

(10) Patent No.: US 6,670,331 B2
(45) Date of Patent: Dec. 30, 2003

(54) 11-O-SUBSTITUTED KETOLIDE DERIVATIVES

(75) Inventors: Ly Tam Phan Phan, Malden, MA (US); Deqiang Niu, Waltham, MA (US); Yat Sun Or, Cambridge, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 10/011,642

(22) Filed: Dec. 4, 2001

(65) Prior Publication Data

US 2003/0114395 A1 Jun. 19, 2003

(51) Int. Cl.$^7$ .................... A61K 31/70; C07H 17/08
(52) U.S. Cl. .................. 514/29; 536/7.2; 536/7.4; 536/18.5
(58) Field of Search .................. 536/7.2, 7.5, 18.5; 514/29

(56) References Cited

U.S. PATENT DOCUMENTS 5,866,549 A * 2/1999 Or et al. .................. 514/29

FOREIGN PATENT DOCUMENTS

| EP | 0 194 833 A2 * | 9/1986 |
| WO | WO 98/38199 | 9/1998 |

OTHER PUBLICATIONS

Agouridas, C. et al., *J. Med. Chem.* 1998, 41, 4080–4100.

* cited by examiner

*Primary Examiner*—Elli Peselev
(74) *Attorney, Agent, or Firm*—Gabiano D. Maccarone; Jason D. Ferrone

(57) ABSTRACT

There are described novel 11-O-substituted ketolide derivatives of clarithromycin analogs and pharmaceutically acceptable compositions comprising a therapeutically effective amount of a compound of the invention in combination with a pharmaceutically acceptable carrier. Also described is a method for treating bacterial infections by administering to a mammal a pharmaceutical composition containing a therapeutically-effective amount of a compound of the invention, and processes for the preparation of such compounds.

11 Claims, No Drawings

11-O-SUBSTITUTED KETOLIDE DERIVATIVES

TECHNICAL FIELD

The present invention relates to novel macrolides having antibacterial activity that are useful in the treatment and prevention of bacterial infections. More particularly, the present invention relates to a novel class of 11-O-substituted ketolide derivatives of clarithromycin macrolides, compositions containing such compounds and methods for using the same, as well as processes for making such compounds.

BACKGROUND OF THE INVENTION

Macrolide antibiotics play a therapeutically important role, particularly with the emergence of new pathogens. Structural differences are related to the size of the lactone ring and to the number and nature (neutral or basic) of the sugars. Macrolides are classified according to the size of the lactone ring (12, 14, 15 or 16 atoms). The macrolide antibiotic family (14-, 15- and 16-membered ring derivatives) shows a wide range of characteristics (antibacterial spectrum, side-effects and bioavailability). Among the commonly used macrolides are erythromycin and clarithromycin. The 3-descladinose-3-oxo-clarithromycin macrolides are known as ketolides. Ketolides have shown enhanced activity towards gram-negative bacteria and macrolide resistant gram-positive bacteria. The search for macrolide compounds which are active against MLSB-resistant strains ($MLS_B$=Macrolides-Lincosamides-type B Streptogramines) has become a major goal, together with retaining the overall profile of the macrolides in terms of stability, tolerance and pharmacokinetics.

SUMMARY OF THE INVENTION

The present invention provides novel 11-O-substituted ketolide derivatives having antibacterial activity and their pharmaceutically acceptable salts, esters and prodrugs thereof. The compounds of the present invention are represented by the general formula (I) as illustrated below.

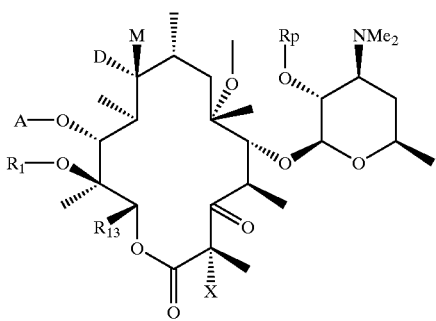

(I)

In formula (I) above,
A is selected from the group consisting of:
(1) $C_1$–$C_6$-alkyl, $C_2$–$C_6$-alkenyl or $C_2$–$C_6$-alkynyl, optionally substituted with one or more substituents selected from the group consisting of:
  a. halogen;
  b. aryl;
  c. substituted aryl;
  d. heteroaryl;
  e. substituted heteroaryl;
  f. —O—$R_5$, where $R_5$ is selected from the group consisting of:
    i. hydrogen;
    ii. aryl;
    iii. substituted aryl;
    iv. heteroaryl; and
    v. substituted heteroaryl;
  g. —O—$C_1$–$C_6$-alkyl-$R_5$, where $R_5$ is as previously defined;
  h. —O—$C_1$–$C_6$-alkenyl-$R_5$, where $R_5$ is as previously defined
  i. —O—$C_2$–$C_6$-alkynyl-$R_5$, where $R_5$ is as previously defined; and
  j. —$NR_6R_7$, where $R_6$ and $R_7$ are each independently selected from hydrogen, $C_1$–$C_6$-alkyl, optionally substituted with one or more substituents selected from the group consisting of halogen, aryl, substituted aryl, heterocyclic and substituted heterocyclic, $C_2$–$C_6$-alkenyl, optionally substituted with one or more substituents selected from the group consisting of halogen, aryl, substituted aryl, heterocyclic and substituted heterocyclic, $C_2$–$C_6$-alkynyl, optionally substituted with one or more substituents selected from the group consisting of halogen, aryl, substituted aryl, heterocyclic and substituted heterocyclic or $R_6R_7$ taken with the nitrogen atom to which they are connected form a 3- to 7-membered ring which may optionally contain one or more hetero functions selected from the group consisting of —O—, —NH—, —N($C_1$–$C_6$-alkyl)—, —N(aryl)-, —N(heteroaryl)-, —S—, —S(O)— and —S(O)$_2$—;
(2) —C(O)—$R_5$, where $R_5$ is as previously defined;
(3) —C(O)—$C_1$–$C_6$-alkyl—$R_5$, where $R_5$ is as previously defined;
(4) —C(O)—$C_2$–$C_6$-alkenyl—$R_5$, where $R_5$ is as previously defined;
(5) —C(O)—$C_2$–$C_6$-alkynyl—$R_5$, where $R_5$ is as previously defined;
(6) —$C_1$–$C_6$-alkyl—M—$R_5$, where M=—OC(O)—, —OC(O)O—, —OC(O)$NR_6$—, —$NR_6$C(O)—, —$NR_6$C(O)O—, —$NR_6$C(O)$NR_7$—, —$NR_6$C(N)$NR_7$—, S(O)$_n$—, where n=0, 1 or 2, and where $R_5$, $R_6$, $R_7$ are as previously defined;
(7) —$C_2$–$C_6$-alkenyl—M—$R_5$ where M=—OC(O)—, —OC(O)O—, —OC(O)$NR_6$—, —$NR_6$C(O)—, —$NR_6$C(O)O—, —$NR_6$C(O)$NR_7$—, —$NR_6$C(N)$NR_7$—, S(O)$_n$—, where n=0, 1 or 2, and where $R_5$, $R_6$, $R_7$ are as previously defined; and
(8) —$C_2$–$C_6$-alkynyl—M—$R_5$ where M=—OC(O)—, —OC(O)O—, —OC(O)$NR_6$—, —$NR_6$C(O)—, —$NR_6$C(O)O—, —$NR_6$C(O)$NR_7$—, —$NR_6$C(N)$NR_7$—, S(O)$_n$—, where n=0, 1 or 2, and where $R_5$, $R_6$, $R_7$ are as previously defined;

$R_1$ is selected from the group consisting of:
(1) hydrogen;
(2) $R_3$, where $R_3$ is $C_1$–$C_6$-alkyl, $C_2$–$C_6$-alkenyl or $C_2$–$C_6$-alkynyl, optionally substituted with one or more substituents selected from the group consisting of:
  a. halogen;
  b. aryl;
  c. substituted aryl;
  d. heteroaryl;
  e. substituted heteroaryl;
  f. —O—$C_1$–$C_6$-alkyl—$R_5$, where $R_5$ is as previously defined;
  g. —$NR_6R_7$, where $R_6$ and $R_7$ are as previously defined.
(3) —C(=O)—$R_4$, where $R_4$ is H or $R_3$ as previously defined;

(4) —C(=O)O—$R_3$, where $R_3$ is as previously defined; and (5) —C(=O)N—$R_6R_7$, where $R_6$ and $R_7$ are as previously defined;

D and M are selected from the group consisting of:
(1) one of D and M is hydrogen and the other is selected from the group consisting of:
  i. hydrogen;
  ii. hydroxy;
  iii. protected hydroxy; and
  iv. —$NR_6R_7$, where $R_6$ and $R_7$ are as previously defined; and
(2) D and M taken together define Y, where Y is selected from the group consisting of:
  a. =O;
  b. =N—OH;
  c. =N—O—$R_8$, where $R_8$ is a $C_1$–$C_6$-alkyl group, optionally substituted with a group selected from an aryl, substituted aryl, heteroaryl, or substituted heteroaryl; and
  d. =N—O—C($R_9$)($R_{10}$)—O—$R_{11}$, where $R_9$ and $R_{10}$ are each independently selected from the group consisting of hydrogen or $C_1$–$C_6$-alkyl, and $R_{11}$ is selected from the group consisting of:
    i. $R_8$, as previously defined;
    ii. —$C_1$–$C_6$-alkyl, optionally substituted with $C_1$–$C_6$-alkoxy; and
    iii. —$C_1$–$C_6$-alkyl—O—$C_1$–$C_6$-alkyl—$R_5$, where $R_5$ is as previously defined;

X is selected from the group consisting of:
(1) hydrogen;
(2) methyl; and
(3) halogen;

$R_{13}$ is selected from:
(1) hydrogen,
(2) $C_1$–$C_6$-alkyl optionally substituted with halogen,
(3) $C_2$–$C_6$-alkenyl,
(4) $C_2$–$C_6$-alkynyl, or
(5) —$CH_2$—R", where R" is selected from hydrogen, $C_1$–$C_6$-alkyl, $C_2$–$C_6$-alkenyl, $C_2$–$C_6$-alkynyl or phenyl, optionally substituted with halogen, or $C_1$–$C_6$-alkyl optionally substituted with $R_5$, where $R_5$ is as defined previously;
(6) —$C_3$–$C_8$-cycloalkyl; and Rp is hydrogen or hydroxy protecting group.

Another embodiment of the present invention pertains to pharmaceutical compositions comprising a therapeutically effective amount of compound(s) of the present invention in combination with a pharmaceutically acceptable carrier and treatment of bacterial infections with such compositions. In yet another embodiment, the present invention pertains to carriers and methods of formulation suitable for use with the compounds and compositions of the present invention. In particular, the compounds and compositions of the present invention have antibacterial activity.

In a further embodiment, the present invention pertains to processes for the preparation of ketolide derivatives of formula (I) above.

DETAILED DESCRIPTION OF THE INVENTION

A first embodiment of the invention is a compound represented by formula I as described above.

Representative compounds of the invention are those selected from the group consisting of:

Compound of formula I: A=—$CH_2CHCH_2$, $R_1$=$R_p$=H, X=H, $R_{13}$=ethyl, and D, M taken together=O;

Compound of formula I: A=—$CH_2CHCH$—(3-quinolyl), $R_1$=$R_p$=H, X=H, $R_{13}$=ethyl, and D, M taken together=O;

Compound of formula I: A=—$CH_2CH_2CH_2$—(3-quinolyl), $R_1$=$R_p$=H, X=H, $R_{13}$=ethyl, and D, M taken together=O;

Compound of formula I: A=—$CH_2CH_2CH_2CH_2$-(4-phenyl-1-imidazolyl), $R_1$=$R_p$=H, X=H, $R_{13}$=ethyl, and D, M taken together=O;

Compound of formula I: A=—$CH_2CH_2CH_2CH_2$-(4-(3-pyridyl)-1-imidazolyl), $R_1$=H, $R_p$=H, X=H, $R_{13}$=ethyl, and D, M taken together=O;

Compound of formula I: A=—$CH_2CH_2CH_2CH_2$-(4-(3-pyridyl)-1-imidazolyl), $R_1$=—C(O)$NH_2$, $R_p$=H, X=H, $R_{13}$=ethyl, and D, M taken together=O;

Compound of formula I: A=—$CH_2CH_2CH_2CH_2CH_2$-(4-phenyl-1-imidazolyl), $R_1$=$R_p$=H, X=H, $R_{13}$=ethyl, and D, M taken together=O;

Compound of formula I: A=—$CH_2CH_2CH_2CH_2CH_2$-(4-(3-pyridyl)-$_1$-imidazolyl), $R_1$=$R_p$=H, X=H, $R_{13}$=ethyl, and D, M taken together=O;

Compound of formula I: A=—$CH_2CH_2CH_2CH_2$-(4-phenyl-1-imidazolyl), $R_1$=—$CH_2CHCH_2$, $R_p$=H, X=H, $R_{13}$=ethyl, and D, M taken together=O;

Compound of formula I: A=—$CH_2CH_2CH_2CH_2$-(4-(3-pyridyl)-1-imidazolyl), $R_1$=—$CH_2CHCH_2$, $R_p$=H, X=H, $R_{13}$=ethyl, and D, M taken together=O;

Compound of formula J: A=—$CH_2CH_2CH_2CH_2$-(4-phenyl-1-imidazolyl), $R_1$=—$CH_2CHCH_2$, $R_p$=H, X=H, $R_{13}$=ethyl, and D, M taken together=O;

Compound of formula I: A=—$CH_2CH_2CH_2CH_2$-(4-(3-pyridyl)-1-imidazolyl), $R_1$=—$CH_2CHCH_2$, $R_p$=H, X=H, $R_{13}$=ethyl, and D, M taken together=O;

Compound of formula I: A=—$CH_2CH_2CH_2CH_2$-(4-(3-pyridyl)-1-imidazolyl), $R_1$=—$CH_2CH_2CH_2$, $R_p$=H, X=F, $R_{13}$=ethyl, and D, M taken together=O;

Compound of formula I: A=—$CH_2CH_2CH_2CH_2$-(4-(3-pyridyl)-1-imidazolyl), $R_1$=—$CH_2CH_2CH_2$, $R_p$=H, X=F, $R_{13}$=ethyl, and D, M taken together=O;

Compound of formula I: A=—$CH_2CH_2CH_2$-(3-quinolyl), $R_1$=H, $R_p$=H, $R_{13}$=ethyl, and D, M taken together=N—OH;

Compound of formula I: A=—$CH_2CH_2CH_2$-(3-quinolyl), $R_1$=H, $R_p$=H, $R_{13}$=ethyl, and D, M taken together=N—$OCH_2OMe$;

Compound of formula I: A=—$CH_2CH_2CH_2$-(3-quinolyl), $R_1$=H, $R_p$=H, $R_{13}$=ethyl, and D, M taken together=O;

Compound of formula I: A=—$CH_2CH_2CH_2CH_2$-(4-quinolyl), $R_1$=H, $R_p$=H, $R_{13}$=ethyl, and D, M taken together=O;

Compound of formula I: A=—$CH_2CH_2CH_2CH_2$-(4-(3-pyridyl)-1H-pyrazolyl), $R_1$=H, $R_p$=H, $R_{13}$=ethyl, and D, M taken together=O;

Compound of formula I: A=—$CH_2CH_2CH_2CH_2$-(1-benzimidazolyl), $R_1$=H, $R_p$=H, $R_{13}$=ethyl, and D, M taken together=O;

Compound of formula I: A=—$CH_2CH_2CH_2CH_2$-(1-(4-azabenzimidazolyl)), $R_1$=H, $R_p$=H, $R_{13}$=ethyl, and D, M taken together=O;

Compound of formula I: A=—$CH_2CH_2CH_2CH_2$-(3-quinolyl), $R_1$=H, $R_p$=H, X=F, $R_{13}$=ethyl, and D, M taken together=O;

Compound of formula I: A=—CH$_2$CH$_2$CH$_2$CH$_2$-(4-quinolyl), R$_1$=H, R$_p$=H, X=F, R$_{13}$=ethyl, and D, M taken together=O;

Compound of formula I: A=—CH$_2$CH$_2$CH$_2$CH$_2$-(4-(3-pyridyl)-1H-pyrazolyl), R$_1$=H, R$_p$=H, X=F, R$_{13}$=ethyl, and D, M taken together=O;

Compound of formula I: A=—CH$_2$CH$_2$CH$_2$CH$_2$-(1-benzimidazolyl), R$_1$=H, R$_p$=H, X=F, R$_{13}$=ethyl, and D, M taken together=O; and Compound of formula I: A=—CH$_2$CH$_2$CH$_2$CH$_2$-(1-(4-azabenzimidazolyl)), R$_1$=H, R$_p$=H, X=F, R$_{13}$=ethyl, and D, M taken together=O.

Definitions

The terms "C$_1$–C$_3$-alkyl" or "C$_1$–C$_6$-alkyl," as used herein, refer to saturated, straight- or branched-chain hydrocarbon radicals containing between one and three or one and six carbon atoms, respectively. Examples of C$_1$–C$_3$ alkyl radicals include methyl, ethyl, propyl and isopropyl, and examples of C$_1$–C$_6$-alkyl radicals include, but are not limited to, methyl, ethyl, propyl, isopropyl, n-butyl, tert-butyl, neopentyl and n-hexyl.

The term "C$_2$–C$_6$-alkenyl," as used herein, refers to straight- or branched-chain hydrocarbon radicals containing between two and six carbon atoms with one or more double bonds in the chain. Examples of C$_2$–C$_6$-alkenyl include, but are not limited to, propenyl, isobutenyl, 1,3-hexadienyl, n-hexenyl, and 3-pentenyl.

The term "C$_2$–C$_6$-alkynyl," as used herein, refers to straight- or branched-chain hydrocarbon radicals containing between two and six carbon atoms with one or more triple bonds in the chain optionally containing one or more double bond. Examples of C$_2$–C$_6$-alkynyl include, but are not limited to, propynyl, isopentynyl, 1,3-hexadiynyl, n-hexynyl, 3-pentynyl, and 1-hexen-3-ynyl.

The term "C$_1$–C$_6$-alkoxy," as used herein, refers to a C$_1$–C$_6$-alkyl group, as previously defined, attached to the parent molecular moiety through an oxygen atom. Examples of C$_1$–C$_6$-alkoxy include, but are not limited to, methoxy, ethoxy, propoxy, isopropoxy, n-butoxy, tert-butoxy, neopentoxy and n-hexoxy.

The term "aryl," as used herein, refers to unsubstituted carbocyclic aromatic groups including, but not limited to, phenyl, 1- or 2-naphthyl and the like.

The term "heteroaryl," as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

The terms "halo" and "halogen," as used herein, refer to an atom selected from fluorine, chlorine, bromine or iodine.

The terms "C$_3$–C$_8$-cycloalkyl-" as used herein, refer to carbocyclic groups of 3 to 8 carbon atoms, such as for example, cyclopropyl, cyclobutyl, cyclopentyl, cyclohexyl, cycloheptyl and cyclooctyl.

The term "heterocyclic," as used herein, refers to heterocycloalkyl and heteroaryl. The term "substituted heterocyclic", as used herein, refers to substituted heterocycloalkyl and substituted heteroaryl.

The term "substituted aryl," as used herein refers to an aryl group as defined herein substituted by independent replacement of one or more of the hydrogen atoms therein with F, Cl, Br, I, OH, NO$_2$, CN, C(O)—C$_1$–C$_6$-alkyl, C(O)-aryl, C(O)-heteroaryl, CO$_2$-alkyl, CO$_2$-aryl, CO$_2$-heteroaryl, CONH$_2$, CONH-C$_1$–C$_6$-alkyl, CONH-aryl, CONH-heteroaryl, OC(O)—C$_1$–C$_6$-alkyl, OC(O)-aryl, OC(O)-heteroaryl, OCO$_2$-alkyl, OCO$_2$-aryl, OCO$_2$-heteroaryl, OCONH$_2$, OCONH-C$_1$–C$_6$-alkyl, OCONH-aryl, OCONH-heteroaryl, NHC(O)—C$_1$–C$_6$-alkyl, NHC(O)-aryl, NHC(O)-heteroaryl, NHCO$_2$-alkyl, NHCO$_2$-aryl, NHCO$_2$-heteroaryl, NHCONH$_2$, NHCONH-C$_1$–C$_6$-alkyl, NHCONH-aryl, NHCONH-heteroaryl, SO$_2$-C$_1$–C$_6$-alkyl, SO$_2$-aryl, SO$_2$-heteroaryl, SO$_2$NH$_2$, SO$_2$NH-C$_1$–C$_6$-alkyl, SO$_2$NH-aryl, SO$_2$NH-heteroaryl, C$_1$–C$_6$-alkyl, C$_3$–C$_6$-cycloalkyl, CF$_3$, CH$_2$CF$_3$, CHCl$_2$, CH$_2$OH, CH$_2$CH$_2$OH, CH$_2$NH$_2$, CH$_2$SO$_2$CH$_3$, aryl, heteroaryl, benzyl, benzyloxy, aryloxy, heteroaryloxy, C$_1$–C$_6$-alkoxy, methoxymethoxy, methoxyethoxy, amino, benzylamino, arylamino, heteroarylamino, C$_1$–C$_3$-alkyl-amino, thio, aryl-thio, heteroarylthio, benzyl-thio, C$_1$–C$_6$-alkyl-thio, or methylthiomethyl.

The term "substituted heteroaryl," as used herein, refers to a heteroaryl group as defined herein substituted by independent replacement of one or more of the hydrogen atoms therein with F, Cl, Br, I, OH, NO$_2$, CN, C(O)—C$_1$–C$_6$-alkyl, C(O)-aryl, C(O)—heteroaryl, CO$_2$-alkyl, CO$_2$-aryl, CO$_2$-heteroaryl, CONH$_2$, CONH—C$_1$–C$_6$-alkyl, CONH-aryl, CONH-heteroaryl, OC(O)—C$_1$–C$_6$-alkyl, OC(O)-aryl, OC(O)-heteroaryl, OCO$_2$-alkyl, OCO$_2$-aryl, OCO$_2$-heteroaryl, OCONH$_2$, OCONH-C$_1$–C$_6$-alkyl, OCONH-aryl, OCONH-heteroaryl, NHC(O)—C$_1$–C$_6$-alkyl, NHC(O)-aryl, NHC(O)-heteroaryl, NHCO$_2$-alkyl, NHCO$_2$-aryl, NHCO$_2$-heteroaryl, NHCONH$_2$, NHCONH—C$_1$–C$_6$-alkyl, NHCONH-aryl, NHCONH-heteroaryl, SO$_2$-C$_1$–C$_6$-alkyl, SO$_2$-aryl, SO$_2$-heteroaryl, SO$_2$NH$_2$, SO$_2$NH—C$_1$–C$_6$-alkyl, SO$_2$NH—aryl, SO$_2$NH-heteroaryl, C$_1$–C$_6$-alkyl, C$_3$–C$_6$-cycloalkyl, CF$_3$, CH$_2$CF$_3$, CHCl$_2$, CH$_2$OH, CH$_2$CH$_2$OH, CH$_2$NH$_2$, CH$_2$SO$_2$CH$_3$, aryl, heteroaryl, benzyl, benzyloxy, aryloxy, heteroaryloxy, C$_1$–C$_6$-alkoxy, methoxymethoxy, methoxyethoxy, amino, benzylamino, arylamino, heteroarylamino, C$_1$–C$_3$-alkyl-amino, thio, aryl-thio, heteroarylthio, benzyl-thio, C$_1$–C$_6$-alkyl-thio, or methylthiomethyl.

"Hydroxy protecting group," as used herein, refers to an easily removable group which is known in the art to protect a hydroxyl group against undesirable reaction during synthetic procedures and to be selectively removable. The use of hydroxy-protecting groups is well known in the art for protecting groups against undesirable reactions during a synthetic procedure and many such protecting groups are known. See, for example, T. H. Greene and P. G. M. Wuts, *Protective Groups in Organic Synthesis,* 3rd edition, John Wiley & Sons, New York (1999). Examples of hydroxy-protecting groups include, but are not limited to, methylthiomethyl, tert-dimethylsilyl, tert-butyldiphenylsilyl, acyl substituted with an aromatic group and the like.

The term "protected hydroxy" refers to a hydroxy group protected with a hydroxy protecting group, as defined above, include for example, benzoyl, acetyl, trimethylsilyl, triethylsilyl, methoxymethyl groups.

The term "aprotic solvent," as used herein, refers to a solvent that is relatively inert to proton activity, i.e., not acting as a proton-donor. Examples include, but are not limited to, hydrocarbons, such as for example, hexane and toluene, and the like, halogenated hydrocarbons, such as, for example, methylene chloride, ethylene chloride, chloroform, and the like, heterocyclic compounds, such as, for example, tetrahydrofuran, N-methylpyrrolidinone, and the like and ethers such as for example, diethyl ether, bis-methoxymethyl ether and the like. Such compounds are well known to those skilled in the art, and it will be apparent to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al., Vol. II, in the Techniques of Chemistry Series, John Wiley & Sons, NY, 1986.

The term "protogenic organic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be apparent to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification*, 4th ed., edited by John A. Riddick et al., Vol. II, in the Techniques of Chemistry Series, John Wiley & Sons, NY, 1986.

Numerous asymmetric centers may exist in the compounds of the present invention. Except where otherwise noted, the present invention contemplates the various stereoisomers and mixtures thereof. Accordingly, whenever a bond is represented by a wavy line, it is intended that a mixture of stereo-orientations or an individual isomer of assigned or unassigned orientation may be present. Further, in those cases where a bond between carbon atoms of the macrolide is a double bond both the -cis and -trans forms are within the scope of the invention as described in this application.

As used herein, the term "pharmaceutically acceptable salt," refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in *J. Pharmaceutical Sciences*, 66: 1–19 (1977), incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptalble salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, Valetta salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals without undue toxicity, irritation, allergic response and the like, commensurate with a reasonable risk/benefit ratio, and effective for their intended use, as well as the zwitterionic forms, where possible, of the compounds of the invention. The term "prodrug" refers to compounds that are rapidly transformed in vivo to yield the parent compound of the above formulae, for example, by hydrolysis in blood. A thorough discussion is provided in T. Higuchi and V. Stella, *Prodrugs as Novel delivery Systems*, Vol. 14 of the A.C.S. Symposium Series and in Edward B. Roche, ed., *Bioreversible Carriers in Drug Design*, American Pharmaceutical Association and Pergamon Press, 1987, both of which are incorporated by reference herein.

Antibacterial Activity

Susceptibility tests can be used to quantitatively measure the in vitro activity of an antimicrobial agent against a given bacterial isolate. Compounds were tested for in vitro antibacterial activity by a micro-dilution method. Minimal Inhibitory Concentration (MIC) was determined in 96 well microtiter plates utilizing the appropriate Mueller Hinton Broth medium (CAMHB) for the observed bacterial isolates. Antimicrobial agents were serially diluted (2-fold) in DMSO to produce a concentration range from about 64 $\mu$g/ml to about 0.03 $\mu$g/ml. The diluted compounds (2 $\mu$l/well) were then transferred into sterile, uninoculated CAMHB (0.2 mL) by use of a 96 fixed tip-pipetting station. The inoculum for each bacterial strain was standardized to 5×10 CFU/mL by optical comparison to a 0.5 McFarland turbidity standard. The plates were inoculated with 10 $\mu$l/well of adjusted bacterial inoculum. The 96 well plates were covered and incubated at 35 +/–2° C. for 24 hours in ambient air environment. Following incubation, plate wells were visually examined by Optical Density measurement for the presence of growth (turbidity). The lowest concentration of an antimicrobial agent at which no visible growth occurs was defined as the MIC. The compounds of the invention generally demonstrated an MIC in the range from about 64 $\mu$g/ml to about 0.03 $\mu$g/ml.

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminun hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), bucally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, powders, capsules, pills, and granules can be prepared with coatings and shells such as enteric coatings and other coatings well known in the pharmaceutical formulating art. They may optionally contain opacifying agents and can also be of a composition whereby they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, bacterial infections are treated or prevented in a patient such as a human or lower mammal by administering to the patient a therapeutically effective amount of a compound of the invention, in such amounts and for such time as is necessary to achieve the desired result. By a "therapeutically effective amount" of a compound of the invention is meant a sufficient amount of the compound to treat bacterial infections, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or other mammal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

Abbreviations

Abbreviations which have been used in the description of the schemes and the examples are as follows: BOC for tert-Butoxycarbonyl; BSA for bis(trimethylsilyl)acetamide; DMAP for 4-N,N-dimethylamino-pyridine; DCC for 1,3-dicyclohexylcarbodiimide; DMF for dimethyl formamide; DMSO for dimethylsulfoxide; dppb for 1,4-bis (diphenylphosphino)butane; dppe for 1,2-bis (diphenylphosphino)ethane; EDC for 1-ethyl-3-(3-dimethylaminopropyl)carbodiimide; EtOAc for ethyl acetate; HMDS for 1,1,1,3,3,3-Hexamethyldisilazane; KHMDS for potassium bis(trimethylsilyl)amide; MeOH for methanol; MOMCl for methoxymethylchloride; NCS for N-Chlorosuccinimide; NMO for N-methylmorpholine N-oxide; PCC for pyridinium chlorochromate; PDC for pyridinium dichromate; TEA for triethylamine; THF for tetrahydrofuran; TPP for triphenylphosphine; TBAF for tetrabutylammonium fluoride; ITA for trifluoroacetic acid; TPAP for tetrapropylammonium perruthenate; Ac for acetyl and Bz for benzoyl.

Synthetic Methods

The compounds and processes of the present invention will be better understood in connection with the following synthetic schemes that are illustrative of the methods by which the compounds of the invention may be prepared. The groups Rp, $R_1$, X, D, M, and A are as defined previously unless otherwise noted below. $R_{13}$ and C-9 position (D, M) can be further derivatized according to the procedures mentioned in PCT publications: WO 00/62783 and WO 98/38199 as well as publications: "Synthetic Modifications of the Erythromycin A Macrolactone: Effects on Biological Activity," Lartey, P. A. and Perun, T. J., Atta-ur-Rabman (Ed.) *Studies in Natural Products Chemistry*, Vol. 13, 1993, and "Recent developments in 14- and 15-membered macrolides," Chu, Daniel T. W., Section Review: Anti-infectives, *Exp. Opin. Invest. Drugs* 1995, 4(2), page 65–94, which are herein incorporated by reference in their entirety for the purpose of the present invention.

Scheme 1:

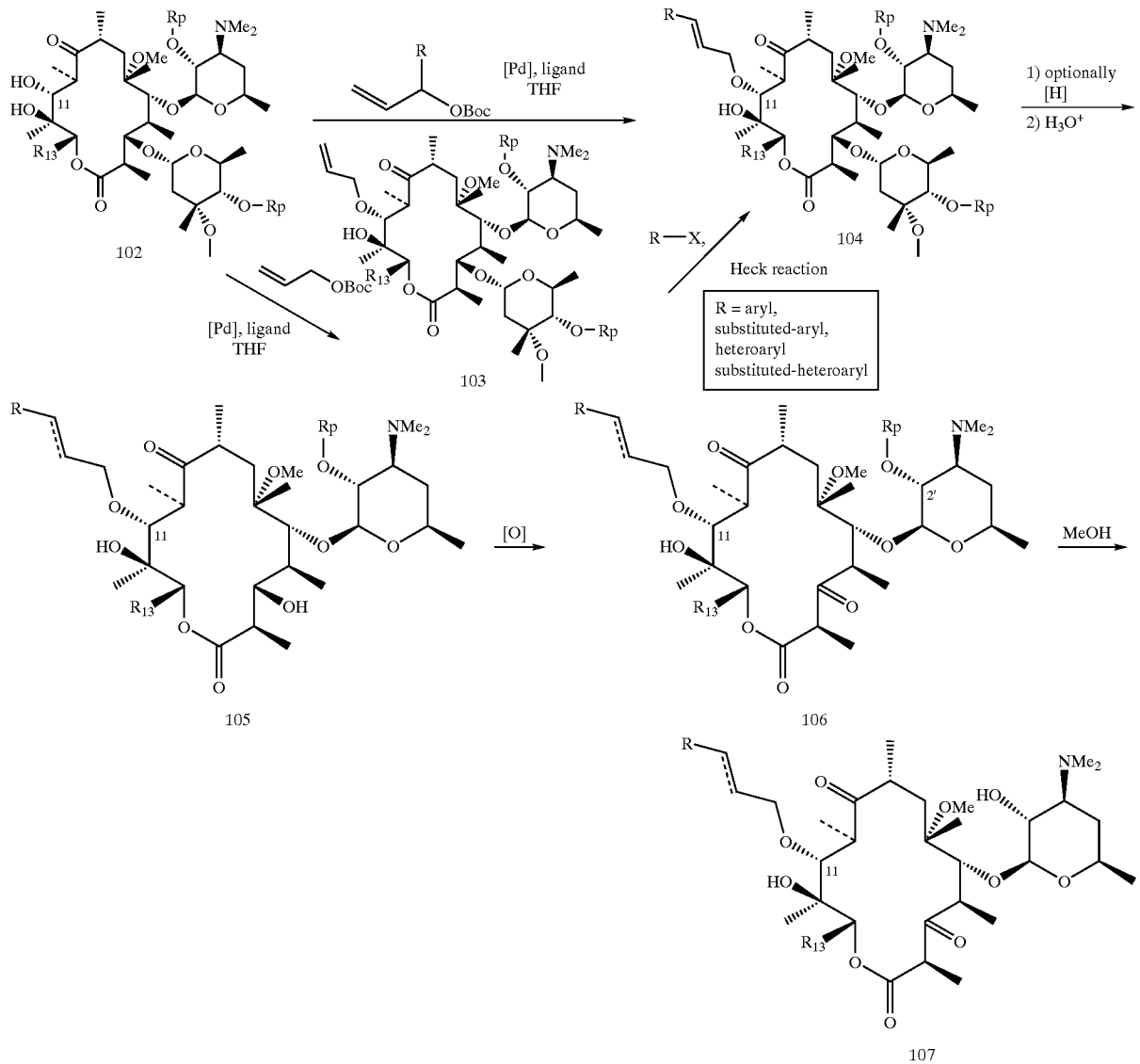

One process of the present invention, dealing with the preparation of the compounds of formula I, comprises the reaction of compound 102 with a tert-butyl allyl carbonate catalyzed by a palladium catalyst [Pd(0) or Pd(II)] with a phosphorus ligand such as dppb, dppe, and the like, in aprotic solvents to provide compound 103 from about room temperature to about 100° C. (see (a) Trost, B. M. *Angew. Chem. Int. Ed. Eng.* 1989, 28, 1179; (b) Heck, Palladium Reagents in Organic Synthesis, Academic Press: New York, 1985, Chapter 1; (c) Tsuji, *Tetrahedron Lett.* 1992, 33, 2987). Compound 103 further reacts with an aryl halide or aryl triflate in the presence of a palladium catalyst [Pd(0) or Pd(II)] with a phosphorus ligand and a base such as TEA, $K_2CO_3$, and the like to provide compound 104 (see (a) Heck, Palladium Reagents in Organic Synthesis, Academic Press: New York, 1985, Chapter 1; (b) Sonogashira, Comprehensive Organic Synthesis, Volume 3, Chapters 2, 4; (c) Sonogashira, *Synthesis* 1977, 777). Alternatively, compound 104 can be obtained similiarly by treating compound 102 with an aryl tert-butyl allyl carbonate catalyzed by a palladium catalyst. Compound 104 was optionally hydrogenated with Palladium on carbon, Palladium black, Platinum oxide or the like under 1–4 atm pressure of hydrogen in an organic solvent such as methanol, ethanol, ethyl acetate or the like at a temperature from about 0° C. to about 50° C. for 1–36 hours to provide the corresponding saturated form in the C11-side chain. Either compounds 104 or the reduced form are then subjected to acid hydrolysis by reacting with dilute aqueous acid (0.1–2N) such as hydrochloric acid, sulfuric acid, trifluoroacetic acid, acetic acid and the like, optionally in an organic solvent such as acetone, acetonitrile, methanol, ethanol or the like, or combinations thereof, at from about 0° C. to about 70° C. for 1–24 hours to provide compound 105. Compound 105 is treated with an oxidizing agent (such as 1,1,1-triacetoxy-1,1-dihydro-1,2-benziodoxol-3(1H)-one, NCS/Me₂S, TPAP/NMO, PCC, PDC and the like) in an aprotic solvent such as methylene chloride, ethylene chloride, THF, chloroform, DMF, acetonitrile or the like at from about 0° C. to about 50° C. for 1–48 hours to provide compound 106 which is further deprotected by treating with methanol at from about room temperature to a refluxing temperature, to remove the hydroxy protecting group at the 2'-position, to provide compound 107.

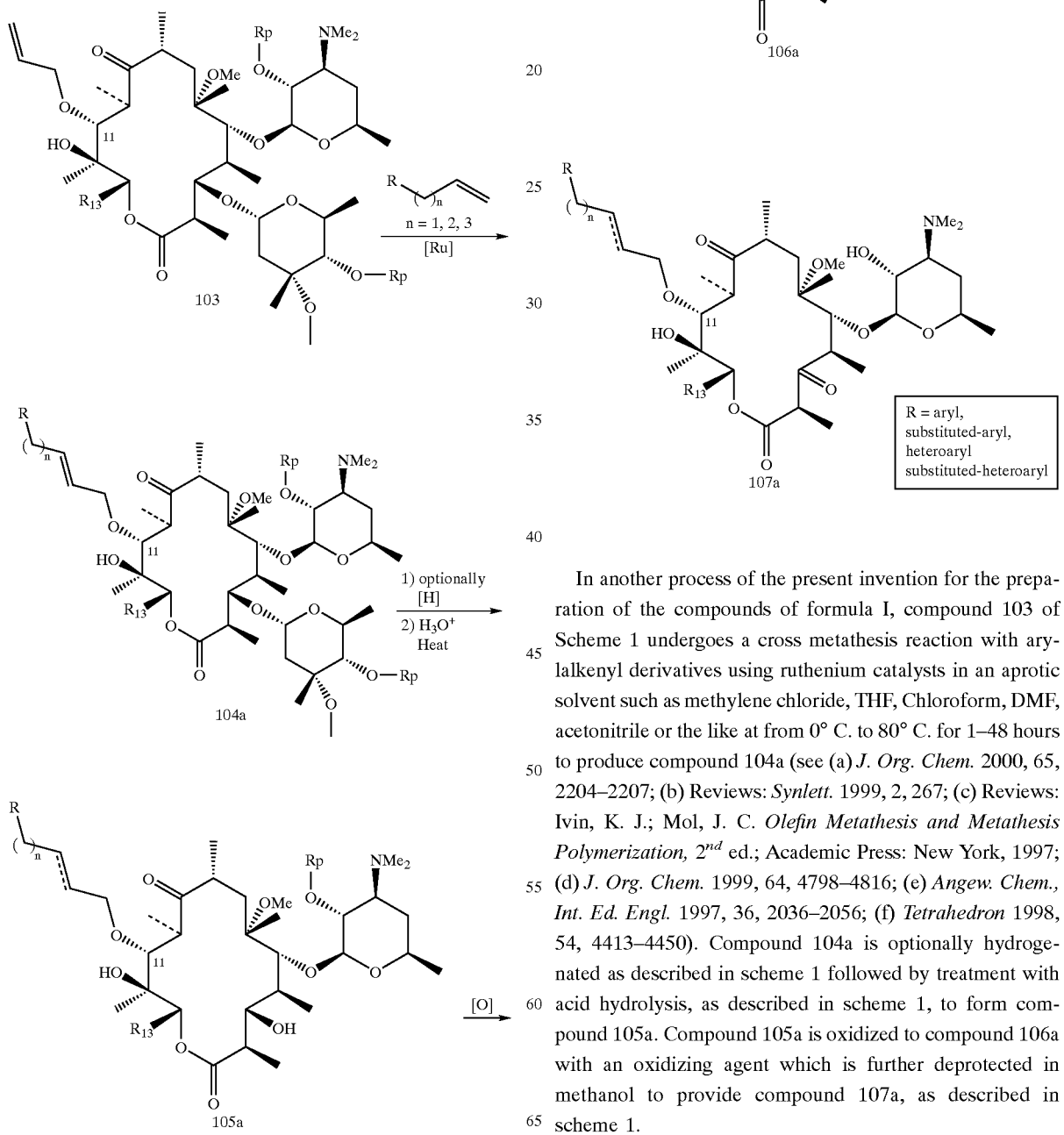

Scheme 2:

In another process of the present invention for the preparation of the compounds of formula I, compound 103 of Scheme 1 undergoes a cross metathesis reaction with arylalkenyl derivatives using ruthenium catalysts in an aprotic solvent such as methylene chloride, THF, Chloroform, DMF, acetonitrile or the like at from 0° C. to 80° C. for 1–48 hours to produce compound 104a (see (a) *J. Org. Chem.* 2000, 65, 2204–2207; (b) Reviews: *Synlett.* 1999, 2, 267; (c) Reviews: Ivin, K. J.; Mol, J. C. *Olefin Metathesis and Metathesis Polymerization*, 2$^{nd}$ ed.; Academic Press: New York, 1997; (d) *J. Org. Chem.* 1999, 64, 4798–4816; (e) *Angew. Chem., Int. Ed. Engl.* 1997, 36, 2036–2056; (f) *Tetrahedron* 1998, 54, 4413–4450). Compound 104a is optionally hydrogenated as described in scheme 1 followed by treatment with acid hydrolysis, as described in scheme 1, to form compound 105a. Compound 105a is oxidized to compound 106a with an oxidizing agent which is further deprotected in methanol to provide compound 107a, as described in scheme 1.

Scheme 3:

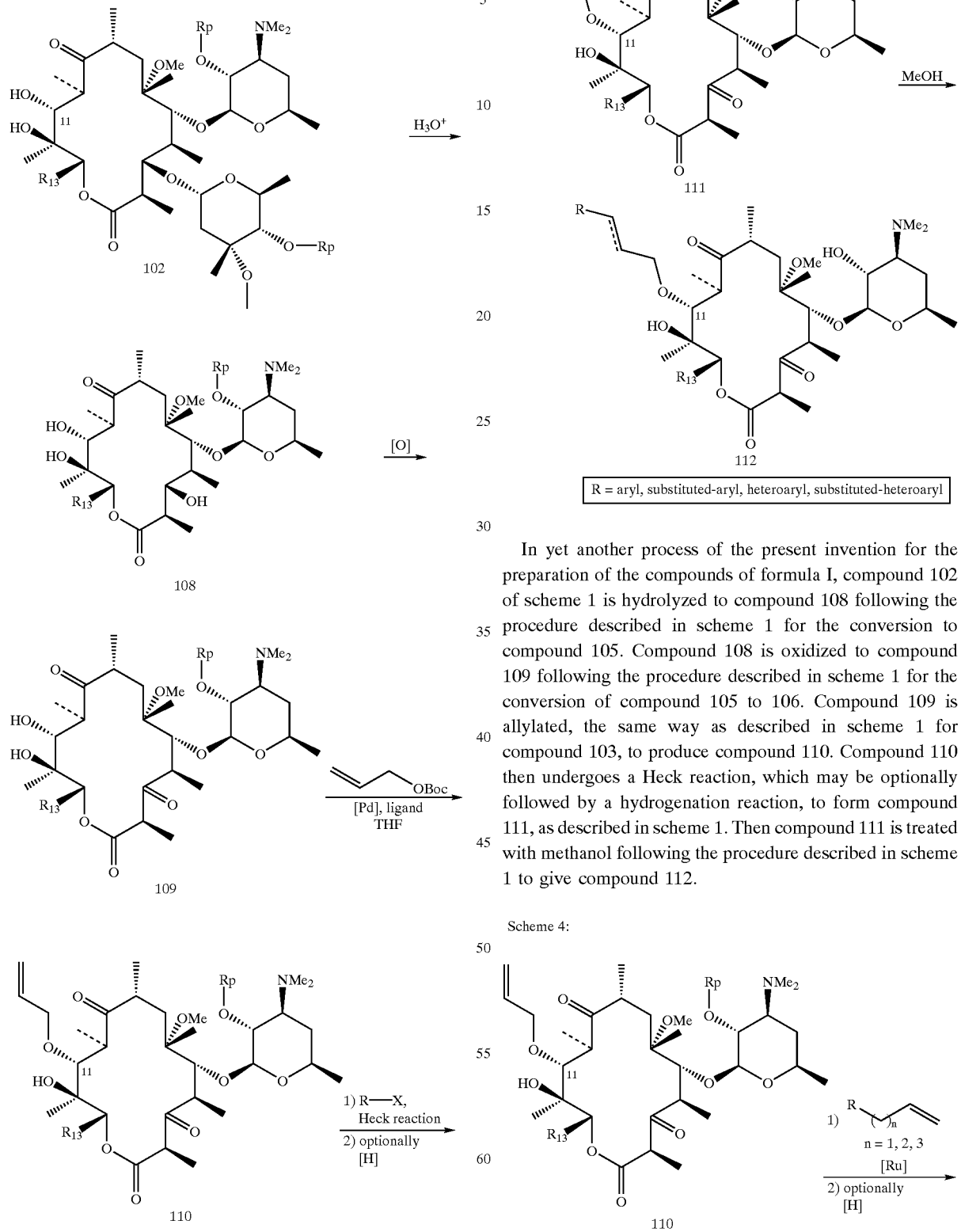

In yet another process of the present invention for the preparation of the compounds of formula I, compound 102 of scheme 1 is hydrolyzed to compound 108 following the procedure described in scheme 1 for the conversion to compound 105. Compound 108 is oxidized to compound 109 following the procedure described in scheme 1 for the conversion of compound 105 to 106. Compound 109 is allylated, the same way as described in scheme 1 for compound 103, to produce compound 110. Compound 110 then undergoes a Heck reaction, which may be optionally followed by a hydrogenation reaction, to form compound 111, as described in scheme 1. Then compound 111 is treated with methanol following the procedure described in scheme 1 to give compound 112.

Scheme 4:

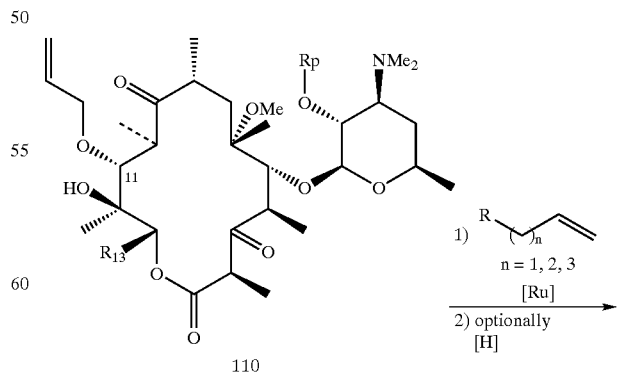

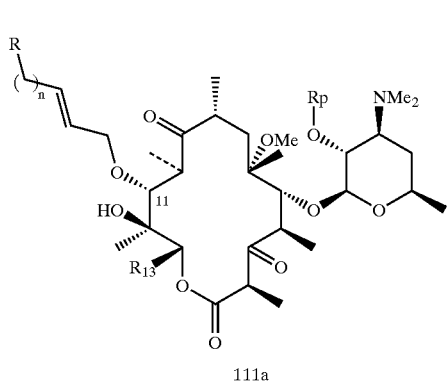

111a

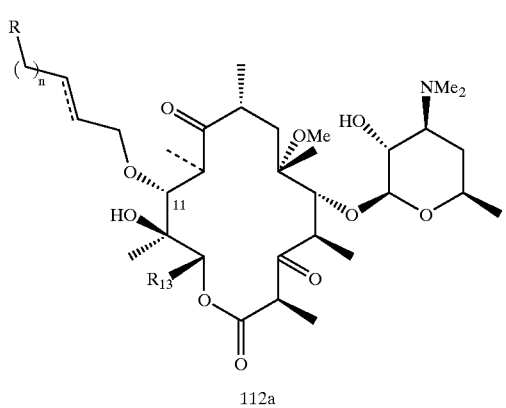

112a

R = aryl, substituted-aryl, heteroaryl, substituted-heteroaryl

In yet another process of the invention for the preparation of the compounds of formula I, compound 110 of scheme 3 undergoes a cross metathesis reaction, which may be optionally followed by a hydrogenation reaction, to form compound 111a as described in scheme 2. Compound 111a is treated with methanol to remove the ester protecting group ($R_p$) followed the procedure described in scheme 1 to give compound 112a.

Scheme 5:

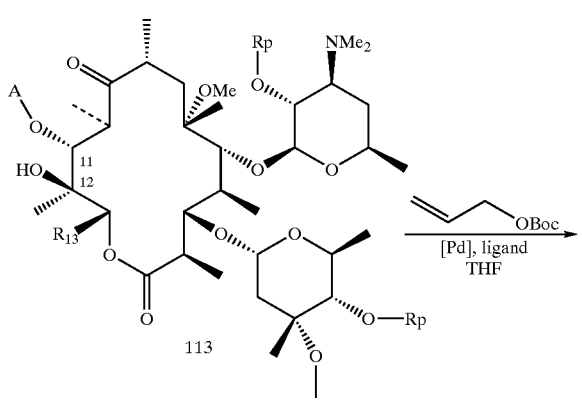

113

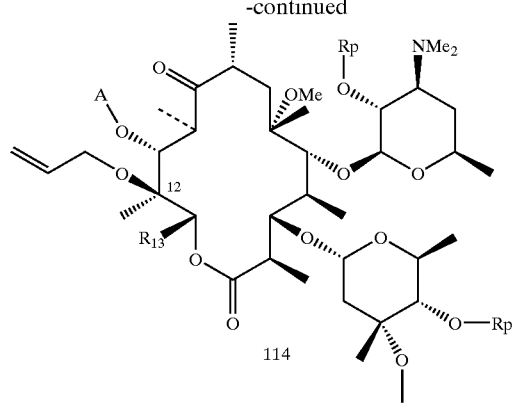

114

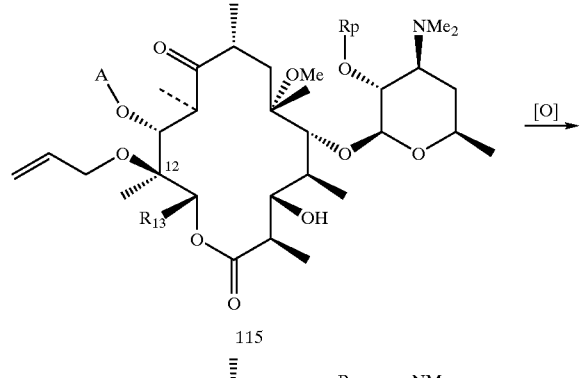

115

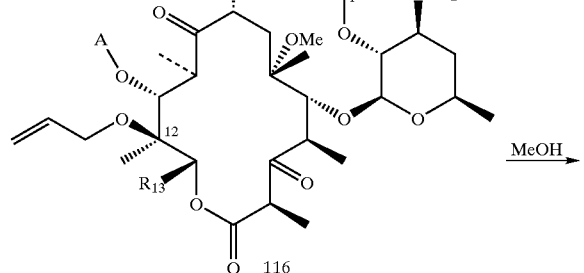

116

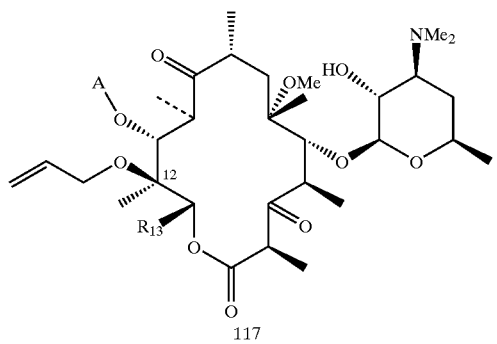

117

In yet another process of the invention for the preparation of the compounds of formula I, compound 113 (where A is as defined in claim 1) undergoes a substitution reaction on the 12-hydroxy group of the macrolide. One of such examples is shown in scheme 5 with a palladium catalyzed allylation reaction as described in scheme 1 except with a longer reaction time and more tert-butyl allyl carbonate. Compound 114 is subjected to acid hydrolysis by reacting with dilute aqueous acid (0.1–2N) such as hydrochloric acid, sulfuric acid, trifluoroacetic acid, acetic acid and the like, optionally in an organic solvent such as acetone, acetonitrile, methanol, ethanol or the like, or combinations thereof, at from about 0° C. to about 70° C. for 1–24 hours to give compound 115 which is oxidized to compound 116 and then is deprotected in methanol to give compound 117 following the procedures described in scheme 1.

of the scope of the invention. Various changes and modifications to the disclosed embodiments will be apparent to those skilled in the art. Such changes and modifications, including without limitation, those relating to the chemical structures, substituents, derivatives, syntheses, formulations and/or methods of the invention may be made without departing from the spirit of the invention and the scope of the appended claims.

Scheme 6:

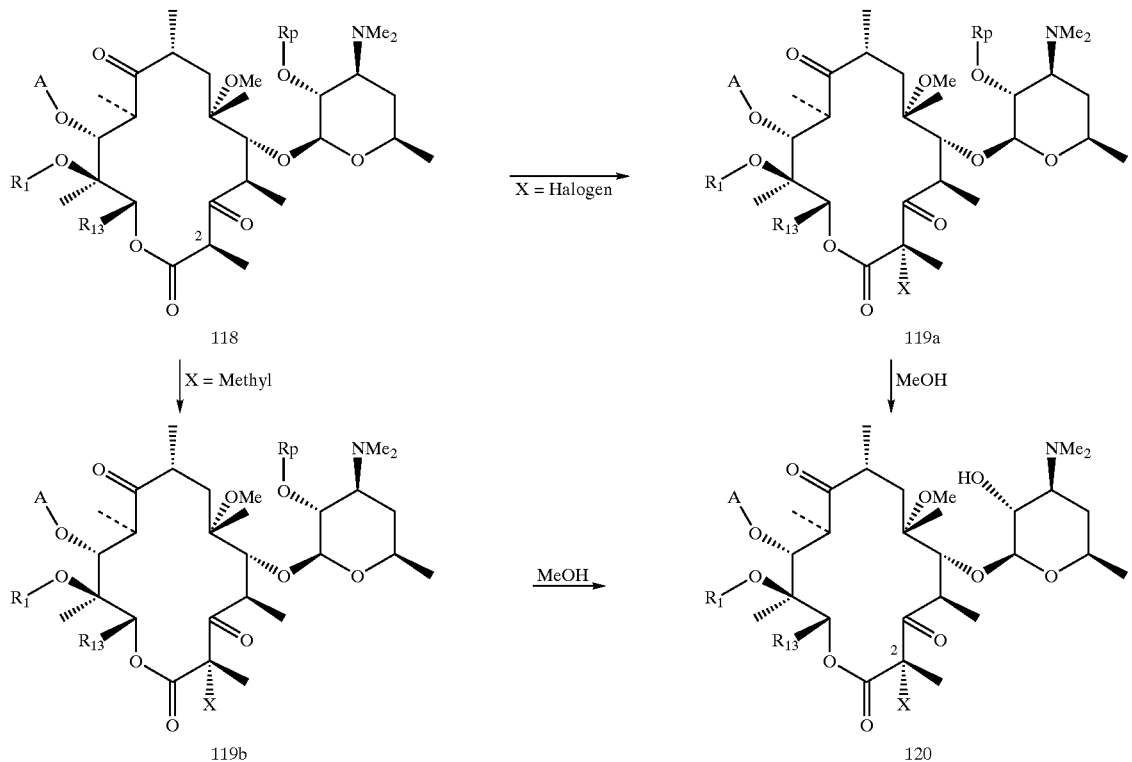

In yet another process of the invention for the preparation of the compounds of formula I, compound 118 (where A, $R_1$, $R_{13}$ $R_p$ are as defined in claim 1) undergoes a substitution reaction at C2 position of the macrolides of the present invention. Compound 118 can be halogenated to form compound 119a by the process in U.S. Pat. No. 6,124,269 and WO 00/62783 which are herein incorporated by reference in its entirety. Also position C2 of compound 118 can be methylated by treatment with methyl iodide in the presence of a base such as $K_2CO_3$, NaOH and the like, with or without a phase transferring catalyst such as tetrabutylammonium iodide or the like in THF, methylene chloride, DMF, DMSO, water and the like or combinations thereof, at from about 0° C. to about 50° C. for 1–24 hours to provide compound 119b. Both compounds 119a and 119b can be deprotected upon treatment with methanol as described in scheme 1 to produce compound 120 where X is as defined in claim 1.

EXAMPLES

The procedures described above for preparing the compounds of formula I of the present invention will be better understood in connection with the following examples which are intended to be illustrative only of, and not limiting Example 1

Compound of Formula I: A=—$CH_2CHCH_2$, $R_1$= $R_p$=H, X=H, $R_{13}$=Ethyl, and D, M Taken Together=O Step 1a. Compound 102 of Scheme 1: $R_p$=Acetyl, $R_{13}$= ethyl;

To a stirring solution of Clarithromycin (3.8 g, 5.0 mmol), acetic anhydride (1.04 mL, 11 mmol) and triethylamine (3.0 mL, 22 mmol) in $CH_2Cl_2$ (15 mL), DMAP (20 mg, cat.) was added at room temperature. The solution was stirred for 12 hours. Then the reaction mixture was diluted with 80 mL ethyl acetate. The resulting solution was washed with water, saturated aqueous $NaHCO_3$ and brine. The organic layer was dried over anhydrous $Na_2SO_4$. The solvent was concentrated under vacuum and the residue was purified on a silica gel column (eluting with $CH_2Cl_2$ containing 4% 2M ammonia solution in methanol) to provide the title compound (3.7 g, 88% yield).

MS (ESI) m/z 832 (M+H)$^+$.

$^{13}$C-NMR (100 MHz, CDCl$_3$): δ 221.3, 175.7, 170.6, 170.1, 100.1, 95.9, 80.3, 78.7, 78.4, 77.8, 76.7, 74.4, 72.9, 72.1, 69.3, 67.4, 63.3(2), 50.7, 49.5, 45.4, 45.0, 40.9, 38.8, 38.7, 37.4, 35.3, 31.3, 21.7, 21.3(2), 21.1, 19.9, 18.5, 18.1, 16.3, 16.1, 14.4, 12.5, 10.7, 9.2.

Step 1b. Compound 103 of Scheme 1: $R_p$=Acetyl, $R_{13}$=ethyl;

The compound from step 1a (1.2 g, 1.4 mmol) in 30 mL anhydrous THF with $Pd_2(dba)_3$ (60 mg, 0.07 mmol) and dppb (57 mg, 0.14 mmol) was degassed at –78° C. Then the solution was warmed up to room temperature under nitrogen. The allyl t-butyl carbonate (0.44 g, 3.0 mmol) was introduced and the reaction solution was heated to reflux slowly. After 2 hours, the reaction was cooled down and solvent was removed under reduced pressure. The residue was purified by chromatography on a silica gel column (eluting with $CH_2Cl_2$ containing 10% 2M ammonia solution in methanol) to provide the title compound (1.35 g, 100%).
MS (ESI) m/z 872 (M+H)$^+$.
$^{13}$C-NMR (100 MHz, $CDCl_3$): δ 217.2, 175.5, 170.6, 170.1, 136.0, 115.8, 99.9, 96.2, 79.4, 79.1, 78.6, 78.1, 77.7, 77.3, 76.2, 73.9, 72.8, 72.2, 67.3, 63.4, 50.6, 49.4, 45.9, 44.9, 40.9, 38.0, 37.8, 37.3, 35.4, 31.3, 21.8, 21.7, 21.3, 21.0, 20.4, 19.5, 18.5, 17.8, 16.2, 13.2, 10.7, 9.3.

Step 1c. Compound 105 (with C11-Unsaturated Side Chain) of Scheme 1: R=H, $R_p$=Acetyl, $R_{13}$=Ethyl;

The compound from step 1b (100 mg, 0.11 mmol) in ethanol (2 mL) and 0.5 mL HCl (4 mL) was heated at 65° C. for 1 hour. Then 10 ml of saturated aqueous $NaHCO_3$ was added and the aqueous layer was extracted 3 times with $CH_2Cl_2$. The combined organic layer was dried over anhydrous $Na_2SO_4$. The solvent was concentrated under vacuum and the residue was purified on a silica gel column (eluting with $CH_2Cl_2$ containing 4% 2M ammonia solution in methanol) to provide the title compound (50 mg, 65%).
MS (ESI) m/z 672 (M+H)$^+$.
$^{13}$C-NMR (100 MHz, $CDCl_3$): δ 216.9, 175.0, 170.1, 135.8, 116.1, 100.0, 80.0, 79.0, 77.9, 77.7, 76.2, 74.2, 71.7, 69.0, 63.4, 49.9, 46.2, 44.3, 40.9, 37.9, 37.4, 36.2, 31.2, 22.0, 21.7, 21.3, 19.8, 19.4, 17.8, 15.3, 13.3, 10.7, 8.1.

Step 1d: Compound of formula I: A=—CH CHCH$_2$ $R_1$=H, $R_p$=Acetyl, X=H, $R_{13}$=Ethyl, and D, M Taken Together=O;

To a cold solution of the compound from step 1c (130 mg, 0.19 mmol) in dry $CH_2Cl_2$ (6 mL) was added DMSO (0.1 mL), EDC (0.15 g, 0.78 mmol), and Pyridine $CF_2CO_2H$ (0.15 g, 0.78 mmol). The reaction was then stirred for 12 hours at room temperature. Then 10 ml of saturated aqueous $NaHCO_3$ was added and the aqueous layer was extracted 3 times with $CH_2Cl_2$. The combined organic layer was dried over anhydrous $Na_2SO_4$. The solvent was concentrated under vacuum and the residue was purified on a silica gel column (eluting with $CH_2Cl_2$ containing 2% 2M ammonia solution in methanol) to provide the title compound (65 mg, 50%) and its 12,9-hemiketal form (about 1:1).
MS (ESI) m/z 670 (M+H)$^+$.
Selected $^{13}$C-NMR (100 MHz, $CDCl_3$): δ 216.9, 205.3, 203.4, 170.2, 170.1, 169.9, 169.8, 135.5, 135.0, 116.2, 115.0, 109.1, 102.2, 101.4.

Step 1e: Compound of Formula I: A=—CH$_2$CHCH$_2$, $R_1$=$R_p$=H, X=H, $R_{13}$=Ethyl, and D, M Taken Together=O The Compound from Step 1d (6.0 mg, 0.01 mmol) in Methanol (5 mL) was Refluxed for 1 hour at 65° C. Concentration gave the title compound (6 mg, 100%).
MS (ESI) m/z 628 (M+H)$^+$.

Example 2

Compound of Formula I: A=—CH$_2$CHCH-(3-quinolyl), $R_1$=$R_p$=H, X=H, $R_{13}$=Ethyl, and D, M Taken Together=O Step 2a: Compound of Formula I: A=—CH$_2$CHCH-(3-quinolyl), $R_1$=H, $R_p$=acetyl, X=H, $R_{13}$=Ethyl, and D, M Taken Together=O;

The Compound from Step 1d (80 mg, 0.12 mmol), 3-bromoquinoline (35 μL, 0.25 mmol), $Pd(OAc)_2$ (2.5 mg, 0.01 mmol), (o-Tolyl)$_3$P (10 mg, 0.03 mmol) and triethyl amine (0.1 mL, 0.7 mmol) were dissolved in 1 mL $CH_3CN$ and the solution was degassed at –40° C. The reaction mixture was warmed up to room temperature and sealed under nitrogen, then was heated at 50° C. for 2 hours, then left at 80° C. for 12 hours. It was diluted with ethyl acetate, washed with saturated aqueous $NaHCO_3$, and dried over anhydrous $Na_2SO_4$. The solvent was evaporated and the residue was purified on a silica gel column (eluting with $CH_2Cl_2$ containing 5% 2M ammonia solution in methanol) to provide the title compound (76 mg, 80%).
MS (ESI) m/z 797 (M+H)$^+$.
Step 2b: Compound of Formula I: A=—CH$_2$CHCH-(3-quinolyl), $R_1$=$R_p$=H, X=H, $R_{13}$=Ethyl, and D, M Taken Together=O The compound from step 2a (70 mg, 0.09 mmol) was processed as described in step 1e and subject to a short silica gel column (eluting with $CH_2Cl_2$ containing 7% 2M ammonia solution in methanol) to provide the title compound (54 mg, 81%).
MS (ESI) m/z 755 (M+H)$^+$.
Selected $^{13}$C-NMR (100 MHz, $CDCl_3$): δ 217.3, 205.1, 170.2, 149.8, 147.7, 132.6, 130.1, 129.6, 129.4, 129.3, 128.4, 128.2, 128.0, 127.0, 103.8.

Example 3

Compound of Formula I: A=—CH$_2$CH$_2$CH$_2$-(3-quinolyl), $R_1$=$R_p$=H, X=H, $R_{13}$=Ethyl, and D, M Taken Together=O The compound from step 2b (20 mg, 0.02 mmol) was was hydrogenated under 1 atm H$_2$ over Pd—C in ethanol at room temperature for 3 hours. The solvent was evaporated under vacuum. Purification on silica gel column (eluting with $CH_2Cl_2$ containing 7% 2M ammonia solution in methanol) gave the title compound (12.3 mg, 60%).
MS (ESI) m/z 757 (M+H)$^+$.
Selected $^{13}$C-NMR (100 MHz, $CDCl_3$): δ 216.0, 203.9, 168.9, 151.0, 145.7, 134.0, 133.6, 133.1, 128.1, 127.2, 126.4, 125.5, 102.4.

Example 4

Compound of Formula I: A=CH$_2$CH$_2$CH$_2$CH$_2$-(4-phenyl-1-imidazolyl), $R_1$=$R_p$H, X=H, $R_{13}$=Ethyl, and D, M Taken Together=O Step 4a. 1-allyl-4-phenylimidazole;

To a solution of 4-Phenylimidazole (2.0 g, 13.9 mmol) in 20 ml DMF was added NaH (60% in mineral oil, 0.7 g, 17.4 mmol) at 0° C. After stirred for 10 minutes, allyl bromide (3.5 mL, 41.4 mmol) was added through a syringe. The reaction was stirred for 12 hours at room temperature, the solvent was evaporated under vacuum and the residue was purified on silica gel column (eluting with ethyl acetate) to provide the title compound (2.2 g, 88%).
MS (ESI) m/z 185 (M+H)$^+$.
$^1$H-NMR (400 MHz, $CDCl_3$): δ 7.73 (2H, d), 7.48 (1H, s), 7.33 (2H, t), 7.22–7.15 (3H, m), 6.00–5.90 (1H, m), 5.28–5.18 (2H, m), 4.53–4.51 (2H, m).
Step 4b. Compound 104a of Scheme 2: $R_p$=acetyl, R=4-phenyl-1-imidazolyl, n=1, $R_{13}$=Ethyl;

To a solution of the compound from step 4a (80 mg, 0.4 mmol) and the compound from step 1b (0.38 g, 0.4 mmol) in $CH_2Cl_2$ (15 mL) was added bis(tricyclohexylphosphino)-3-methyl-2-buten-ylidene ruthenium (IV) dichloride (64 mg, 0.08 mmol). The solution was refluxed for 16 hours. The solvent was removed under vacuum and the residue was purified on silica gel column (eluting with acetone: hexanes/ 3:2) to provide the title compound (0.18 g, 40%).
MS (ESI) m/z 1028 (M+H)$^+$.
Step 4c. Compound 105a (with C11-Saturated Side Chain) of Scheme 2: $R_p$=Acetyl, R=4-phenyl-1-imidazolyl, n=1, $R_{13}$=Ethyl;

The product from step 4b (140 mg) was hydrogenated under 1 atm $H_2$ over Pd—C in ethanol for 16 hours. The solvent was evaporated under vacuum. Purification on silica gel column (eluting with ethyl actate to ethyl actate with 5% triethylamine) gave the title compound (110 mg, 79%).
MS (ESI) m/z 1030 (M+H)$^+$.
$^3$C-NMR (100 MHz, CDCl$_3$): δ 217.7, 175.6, 170.5, 170.1, 142.2, 137.6, 134.6, 128.6, 126.6, 124.9, 115.0, 99.8, 96.2, 79.3, 79.1, 78.6, 78.1, 77.6, 76.4, 76.2, 72.8, 72.2, 70.9, 67.3, 63.39, 63.36, 60.5, 50.6, 49.4, 46.8, 46.0, 44.8, 40.9, 37.9, 37.8, 37.2, 35.4, 31.2, 27.6, 27.2, 21.7, 21.2, 21.0, 20.4, 19.5, 18.5, 14.3, 13.2, 10.7, 9.3.

The above compound (76 mg, 0.074 mmol) was heated in 2 mL 0.2N HCl at 60° C. for 2 hours. Then neutralized with sodium bicarbonate, and extracted with CH$_2$Cl$_2$. The organic solution was dried over anhydrous Na$_2$SO$_4$ and concentrated under vacuum. The residue was purified on a silica gel column (eluting with 5% triethylamine in ethyl acetate) to provide the title compound (45 mg, 75%).
MS (ESI) m/z 830 (M+H)$^+$.
$^{13}$C-NMR (100 MHz, CDCl$_3$): δ 217.4, 175.2, 170.1, 142.3, 137.6, 134.5, 128.7, 126.7, 124.9, 115.0, 100.0, 79.9, 79.0, 77.8, 77.5, 76.8, 76.2, 71.7, 71.2, 69.0, 63.4, 49.8, 46.9, 46.3, 44.4, 40.9, 37.9, 37.4, 36.2, 31.2, 27.7, 27.3, 21.7, 21.3, 19.8, 19.4, 17.8, 15.3, 13.4, 10.7, 8.2.
Step 4d. Compound of Formula I: A=—CH$_2$CH$_2$CH$_2$CH$_2$-(4-phenyl-1-imidazolyl), R$_1$=H, R$_p$=acetyl, X=H, R$_{13}$=Ethyl, and D, M Taken Together=O;

To a solution of the compound from step 4c (30 mg, 0.04 mmol), NMO (16 mg, 0.12 mmol) in methylene chloride (10 mL) was added 4 A molecular sieves (30 mg). After stirred for 5 minutes, 2 mg TPAP was added and the reaction mixture was stirred for 2 hours at room temperature. The solvent was then evaporated under vacuum. The residue was purified on a silica gel column (eluting with acetone) to provide the title compound (26 mg, 87%).
MS (ESI) m/z 828 (M+H)$^+$.
Step 4e. Compound of Formula I: A=—CH$_2$CH$_2$CH$_2$CH$_2$-(4-phenyl-1-imidazolyl), R$_1$=H, R$_p$=H, X=H, R$_{13}$=Ethyl, and D, M Taken Together=O.

A solution of the compound from step 4d (26 mg, 0.03 mmol) in methanol (5 mL) was heated at 60° C. for 1.5 hours. The solvent was evaporated under vacuum. Purification on a silica gel column (eluting with 10% methanol in methylene chloride) gave the desired product (19 mg, 74%).
MS (ESI) m/z 786 (M+H)$^+$.
$^3$C-NMR (100 MHz, CDCl$_3$): δ 217.4, 205.1, 170.2, 142.3, 137.6, 134.5, 128.8, 126.8, 124.9, 114.9, 103.6, 78.6, 77.4, 75.9, 71.2, 70.4, 69.6, 66.2, 53.605, 51.3, 49.9, 46.9, 40.5, 27.7, 27.3, 21.4, 21.2, 20.1, 19.1, 15.0, 13.0, 11.3, 10.9.

Example 5

Compound of Formula I: A=—CH$_2$CH$_2$CH$_2$CH$_2$-(4-(3-pyridyl)-1-imidazolyl), R$_1$=H, R$_p$=H, X=H, R$_{13}$=Ethyl, and D, M Taken Together=O Step 5a. 1-allyl-4-(3-pyridyl)-imidazole;

4-(3-pyridyl)-imidazole is processed as described in step 4a to provide the title compound.
Step 5b. Compound 104a of Scheme 2: R$_p$=acetyl, R=4-(3-pyridyl)-1-imidazolyl n=1, R$_{13}$=Ethyl;

The compound from step 5a is processed as described in step 4b to provide the title compound.
Step 5c. Compound 105a (with C11-Saturated Side Chain) of Scheme 2: R$_p$=Acetyl, R=4-(3-pyridyl)-1-imidazolyl, n=1, R$_{13}$=Ethyl;

The compound from step 5b is processed as described in step 4c to provide the title compound.
Step 5d. Compound of Formula I: A=—CH$_2$CH$_2$CH$_2$CH$_2$-(4-(3-pyridyl)-1-imidazolyl), R$_1$=H, R$_p$=Acetyl, X=H, R$_{13}$=Ethyl, and D, M Taken Together=O;

The compound from step 5c is processed as described in step 4d to provide the title compound.
Step 5e. Compound of Formula I: A=—CH$_2$CH$_2$CH$_2$CH$_2$-(4-(3-pyridyl)-1-imidazolyl), R$_1$=H, R$_p$=H, X=H, R$_{13}$=Ethyl, and D, M Taken Together=O.

The compound from step 5d is processed as described in step 4e to provide the title compound.

Example 6

Compound of Formula I: A=—CH$_2$CH$_2$CH$_2$CH$_2$-(4-(3-pyridyl)-1-imidazolyl), R$_1$=C(O)NH$_2$, R$_p$=Acetyl, X=H, R$_{13}$=Ethyl, and D, M Taken Together=O Step 6a. Compound of Formula I: A=—CH$_2$CH$_2$CH$_2$CH$_2$-(4-(3-pyridyl)-1-imidazolyl), R$_1$=C(O)NH$_2$, R$_p$=Acetyl, X=H, R$_{13}$=Ethyl, and D, M Taken Together=O;

The compound from step 5d is treated with N-trimethylsilylisocyanate in methylene chloride at the presence of triethylamine and CuCl for 4 hours at room temprature to provide the title compound.
Step 6b. Compound of Formula I: A=—CH$_2$CH$_2$CH$_2$CH$_2$-(4-(3-pyridyl)-1-imidazolyl), R$_1$=C(O)NH)$_2$, R$_p$=H, X=H, R$_{13}$=Ethyl, and D, M Taken Together=O.

The compound from step 6a is processed as described in step 4e to provide the title compound.

Example 7

Compound of Formula I: A=—CH$_2$CH$_2$CH$_2$CH$_2$CH$_2$-(4-phenyl-1-imidazolyl), R$_1$=R$_p$=H, X=H, R$_{13}$=Ethyl, and D, M Taken Together=O Step 7a. 1-(3-butenyl)-4-phenylimidazole;

To a solution of 4-phenylimidazole (1.45 g, 10.0 mmol) in 10 mL DMF was added NaH (60% in mineral oil, 0.5 g, 12.5 mmol) at 0° C. After stirred for 10 minutes, 3-butenyl bromide (2.7 g, 20.0 mmol) was added through a syringe. After the reaction was stirred for 12 hours at room temperature, the solvent was evaporated under vacuum and the residue was purified on silica gel column (eluting with ethyl acetate) to provide the title compound (1.4 g, 70%).
MS (ESI) m/z 199 (M+H)$^+$.
Step 7b. Compound 104a of Scheme 2: R$_p$=Acetyl, R=4-phenyl-1-imidazolyl, n=2, R$_{13}$=Ethyl;

To a solution of the compound from step 7a (0.14 g, 0.7 mmol) and the compound from step 1b (0.25 g, 0.29 mmol) in CH$_2$CH$_2$ (15 mL) was added bis(tricyclohexylphosphino) benzylidine ruthenium (IV) dichloride (50 mg, 0.06 mmol). The solution was refluxed for 16 hours. The solvent was removed under vacuum and the residue was purified on silica gel column (eluting with acetone: hexanes/1:1) to provide the title compound (0.22 g, 72%).
MS (ESI) m/z 1042 (M+H)$^+$.
Step 7c. Compound 105a (with 11-Saturated Side Chain) of Scheme 2: R$_p$=Acetyl, R=4-phenyl-1-imidazolyl, n=2, R$_{13}$=Ethyl;

The product from step 7b (140 mg) was hydrogenated under 1.5 atm H$_2$ over Pd—C in ethanol at room temperature for 16 hours. The solvent was evaporated under vacuum. Purification on silica gel column (eluting with acetone: hexanes/1:1) gave the title compound (130 mg, 93%).
MS (ESI) m/z 1044 (M+H)$^+$.

The above compound is treated with 0.2N HCl at 60° C. for 2 hours following the procedure described in step 4c to provide the title compound.

Step 7d. Compound of Formula I: A=—CH$_2$CH$_2$CH$_2$CH$_2$CH$_2$-(4-phenyl-1-imidazolyl), R$_1$=H, R$_p$=Acetyl, X=H, R$_{13}$=Ethyl, and D, M Taken Together=O;

The compound from step 7c is converted to the title compound following the procedure described in step 4d.

Step 7e. Compound of Formula I: A=—CH$_2$CH$_2$CH$_2$CH$_2$CH$_2$-(4-phenyl-1-imidazolyl), R$_1$=H, R$_p$=H, X=H, R$_{13}$=Ethyl, and D, M Taken Together=O.

The compound from step 7d is converted to the title compound following the procedure described in step 4e.

Example 8

Compound of Formula I: A=—CH$_2$CH$_2$CH$_2$CH$_2$CH$_2$-(4-(3-pyridyl)-1-imidazolyl), R$_1$=R$_p$=H, X=H, R$_{13}$=Ethyl, and D, M Taken Together=O Step 8a. 1-(3-butenyl)-4-(3-pyridyl)-imidazole;

The title compound is produced according to the procedure described in step 7a except substituting 4-(3-pyridyl)-imidazole for 4-phenylimidazole.

Step 8b. Compound 104a of Scheme 2: R$_p$=Acetyl, R=-(4-(3-pyridyl)-1-imidazolyl), n=2, R$_{13}$=Ethyl;

The compound from step 8a is reacted with the compound from step 1b to give the title compound following the procedure described in step 4b.

Step 8c. Compound 105a (with 11-Saturated Side Chain) of Scheme 2: R$_p$=Acetyl, R=4-(3-pyridyl)-1-imidazolyl, n=2, R$_{13}$=Ethyl;

The title compound is produced according to the procedure described in step 4c substituting the compound from step 8b for the compound from step 4b.

Step 8d. Compound of Formula I: A=—CH$_2$CH$_2$CH$_2$CH$_2$CH$_2$-(4-(3-pyridyl)-1-imidazolyl), R$_1$=H, R$_p$=Acetyl, X=H, R$_{13}$=Ethyl, and D, M Taken Together=O;

The compound from step 8c is converted to the title compound following the procedure described in step 4d.

Step 8e. Compound of Formula I: A=—CH$_2$CH$_2$CH$_2$CH$_2$CH$_2$-(4-(3-pyridyl)-1-imidazolyl) R$_1$=H, R$_p$=H, X=H, R$_{13}$=Ethyl, and D, M Taken Together=O.

The compound from step 8d is converted to the title compound following the procedure described in step 4e.

Example 9

Compound of Formula I: A=—CH$_2$CH$_2$CH$_2$CH$_2$-(4-phenyl-1-imidazolyl), R$_1$=—CH$_2$CHCH$_2$, R$_p$=H, X=H, R$_{13}$=Ethyl, and D, M Taken Together=O Step 9a. Compound 114 of Scheme 5: A=—CH$_2$CH$_2$CH$_2$CH$_2$-(4-phenyl-1-imidazolyl), R$_p$=Acetyl, R$_{13}$=Ethyl;

The product from step 4b (200 mg) was hydrogenated under 1.5 atm H$_2$ over Pd—C in ethanol for 16 hours. The solvent was evaporated under vacuum. Purification on silica gel column (eluting with ethyl actate to ethyl actate with 5% triethylamine) gave the title compound (200 mg, 100%). MS (ESI) m/z 1030 (M+H)$^+$.

The above compound (200 mg, 0.19 mmol) with Pd$_2$(dba)$_3$ (20 mg, 0.02 mmol) and dppb (18 mg, 0.04 mmol) were dissolved in 15 mL anhydrous THF and the solution was degassed at −78° C. The solution was warmed up to room temperature under nitrogen. And allyl t-butyl carbonate reagent (1.0 mL, excess) was introduced. The reaction mixture was heated for 48 hours before the reaction was cooled down. The solvent was removed under reduced pressure. The residue was purified by chromatography on a silica gel column (eluting with acetone: hexanes/70:30) to provide the title compound (0.12 g, 48%)
MS (ESI) m/z 1070 (M+H)$^+$.

Step 9b. Compound 115 of Scheme 5: A=—CH$_2$CH$_2$CH$_2$CH$_2$-(4-phenyl-1-imidazolyl), R$_p$=Acetyl, R$_{13}$=Ethyl;

The compound from step 9a (120 mg, 0.11 mmol) was heated in 6 mL 0.2N HCl at 60° C. for 2 hours. The reaction was cooled down to room temperature and neutralized with sodium bicarbonate, and extracted with CH$_2$Cl$_2$. The organic solution was dried over anhydrous Na$_2$SO$_4$ and concentrated under vacuum. The residue was purified on a silica gel column (eluting with acetone: hexanes/1:1) to provide the title compound (50 mg).
MS (ESI) m/z 870 (M+H)$^+$.

Step 9c. Compound of Formula I: A=—CH$_2$CH$_2$CH$_2$CH$_2$-(4-phenyl-1-imidazolyl), R$_1$=—CH$_2$CH$_2$CHCH$_2$, R$_p$=Acetyl, X=H, R$_{13}$=Ethyl, and D, M Taken Together=O;

The compound from step 9b was converted to the title compound (20 mg, 40%) following the procedure described in step 4d.
MS (ESI) m/z 868 (M+H)$^+$.

Step 9d. Compound of Formula I: A=—CH$_2$CH$_2$CH$_2$CH$_2$-(4-phenyl-1-imidazolyl), R$_1$=—CH$_2$CH$_2$CH$_2$, R$_p$=H, X=H, R$_{13}$=Ethyl, and D, M Taken Together=O.

The compound from step 9c was converted to the title compound (6.5 mg, 100%) following the procedure described in step 4e.
MS (ESI) m/z 826 (M+H)$^+$.

Example 10

Compound of Formula I: A=—CH$_2$CH$_2$CH$_2$CH$_2$CH$_2$-(4-(3-pyridyl)-1-imidazolyl), R$_1$=—CH$_2$CHCH$_2$, R$_p$=H, X=H, R$_{13}$=Ethyl, and D, M Taken Together=O Step 10a. Compound 114 of Scheme 5: A=—CH$_2$CH$_2$CH$_2$CH$_2$-(4-(3-pyridyl)-1-imidazolyl), R$_p$=Acetyl, R$_{13}$=Ethyl;

The title compound is obtained following the procedure described in step 9a substituting the compound from step 5b for the compound from step 4b.

Step 10b. Compound 115 of Scheme 5: A=—CH$_2$CH$_2$CH$_2$CH$_2$-(4-(3-pyridyl)-1-imidazolyl), R$_p$=Acetyl, R$_{13}$=Ethyl;

The compound from step 10a is converted to the title compound following the procedure described in step 9b.

Step 10c. Compound of Formula I: A=—CH$_2$CH$_2$CH$_2$CH$_2$-(4-(3-pyridyl)-1-imidazolyl), R$_1$=—CH$_2$CHCH$_2$R$_p$=Acetyl, X=H, R$_{13}$=Ethyl, and D, M Taken Together=O;

The compound from step 10b is converted to the title compound following the procedure described in step 4d.

Step 10d. Compound of Formula I: A=—CH$_2$CH$_2$CH$_2$CH$_2$-4-(3-pyridyl)-1-imidazolyl), R$_1$=—CH$_2$CHCH$_2$, R$_p$=H, X=H, R$_{13}$=Ethyl, and D, M Taken Together=O.

The compound from step 10c is converted to the title compound following the procedure described in step 4e.

Example 11

Compound of Formula I: A=—
CH$_2$CH$_2$CH$_2$CH$_2$CH$_2$-(4-phenyl-1-imidazolyl),
R$_1$=—CH$_2$CHCH$_2$, R$_p$=H, X=H, R$_{13}$=Ethyl, and D,
M Taken Together=O Step 11a. Compound 114 of scheme 5: A=—CH$_2$CH$_2$CH$_2$CH$_2$CH$_2$-(4-phenyl-1-imidazolyl), R$_p$=Acetyl, R$_{13}$=Ethyl;

The title compound was obtained (70 mg, 50% two steps) following the procedure described in step 9a substituting the compound from step 7b for the compound from step 4b. MS (ESI) m/z 1084 (M+H)$^+$.

Step 11b. Compound 115 of scheme 5: A=—CH$_2$CH$_2$CH$_2$CH$_2$CH$_2$-(4-phenyl-1-imidazolyl), R$_p$=Acetyl, R$_{13}$=Ethyl;

The compound from step 11a was converted to the title compound (35 mg, 62%) following the procedure described in step 9.
MS (ESI) m/z 884 (M+H)$^+$.

Step 11c. Compound of Formula I: A=—CH$_2$CH$_2$CH$_2$CH$_2$CH$_2$-(4-phenyl-1-imidazolyl), R$_1$=—CH$_2$CHCH$_2$, R$_p$=Acetyl, X=H, R$_{13}$=Ethyl, and D, M Taken Together=O;

The compound from step 11b was converted to the title compound following the procedure described in step 4d.
MS (ESI) m/z 882 (M+H)$^+$.

Step 11d. Compound of Formula I: A=—CH$_2$CH$_2$CH$_2$CH$_2$CH$_2$-(4-phenyl-1-imidazolyl), R$_1$=—CH$_2$CHCH$_2$, R$_p$=H, X=H, R$_{13}$=Ethyl, and D, M Taken Together=O.

The title compound is produced (19 mg, 57% two steps) according to the procedure described in step 4e substituting the compound from step 11c for the compound from step 4d.
MS (ESI) m/z 840 (M+H)$^+$.

Example 12

Compound of Formula I: A=—
CH$_2$CH$_2$CH$_2$CH$_2$CH$_2$CH$_2$-(4-(3-pyridyl)-1-imidazolyl), R$_1$=—CH$_2$CHCH$_2$ R$_p$=H, X=H, R$_{13}$=
Ethyl, and D, M Taken Together=O Step 12a. Compound 114 of Scheme 5: A=—CH$_2$CH$_2$CH$_2$CH$_2$CH$_2$-(4-(3-pyridyl)-1-imidazolyl), R$_p$=Acetyl, R$_{13}$=Ethyl;

The compound from step 8b is converted to the title compound following the procedure described in step 9a.

Step 12b. Compound 115 of Scheme 5: A=—CH$_2$CH$_2$CH$_2$CH$_2$CH$_2$-(4-(3-pyridyl)-1-imidazolyl), R$_p$=Acetyl, R$_{13}$=Ethyl;

The compound from step 12a is converted to the title compound following the procedure described in step 9b.

Step 12c. Compound of Formula I: A=—CH$_2$CH$_2$CH$_2$CH$_2$CH$_2$-(4-(3-pyridyl)-1-imidazolyl), R$_1$=—CH$_2$CHCH$_2$, R$_p$=Acetyl, X=H, R$_{13}$=Ethyl, and D, M Taken Together=O;

The compound from step 12b is converted to the title compound following the procedure described in step 4d.

Step 12d. Compound of formula I: A=—CH$_2$CH$_2$CH$_2$CH$_2$CH$_2$-(4-(3-pyridyl)-1-imidazolyl), R$_1$=—CH$_2$CH$_2$CH$_2$, R$_p$=H, X=H, R$_{13}$=Ethyl, and D, M Taken Together=O.

The compound from step 12c is converted to the title compound following the procedure described in step 4e.

Example 13

Compound of Formula I: A=—
CH$_2$CH$_2$CH$_2$CH$_2$CH$_2$-(4-(3-pyridyl)-1-imidazolyl),
R$_1$=—CH$_2$CHCH$_2$, R$_p$=H, X=F, R$_{13}$=Ethyl, and D,
M Taken Together=O Step 13a. Compound of formula I: A=—CH$_2$CH$_2$CH$_2$CH$_2$-(4-(3-pyridyl)-1-imidazolyl), R$_1$=—CH$_2$CHCH$_2$, R$_p$=Acetyl, X=F, R$_{13}$=Ethyl, and D, M Taken Together=O;

The compound from step 10c is dissolved in DMF and cooled to 0° C. NaH is added and the mixture is stirred for 30 minutes. To this solution is added N-fluorobenzenesulfonimide and the resulting solution is stirred at 0° C. for 3 hours. The mixture is taken up to Ethyl acetate and washed with sodium bicarbonate, brine and water. The organic layer is dried over Na$_2$SO$_4$ and concentrated under vacuum. The residue is purified by chromatography on a silica gel column to give the title compound.

Step 13b. Compound of Formula I: A=—CH$_2$CH$_2$CH$_2$CH$_2$-(4-(3-pyridyl)-1-imidazolyl), R$_1$=—CH$_2$CHCH$_2$, R$_p$=H, X=F, R$_{13}$=Ethyl, and D, M Taken Together=O.

The compound from step 13a is converted to the title compound following the procedure described in step 4e.

Example 14

Compound of Formula I: A=—CH$_2$
CH$_2$CH$_2$CH$_2$-(4-(3-pyridyl)-1-imidazolyl),
R$_1$=—CH$_2$CHCH$_2$, R$_p$=H, X=F, R$_{13}$=Ethyl, and D,
M Taken Together=O Step 14a. Compound of Formula I: A=—CH$_2$CH$_2$CH$_2$CH$_2$CH$_2$-(4(3-pyridyl)-1-imidazolyl), R$_1$=—CH$_2$CHCH$_2$, R$_p$=Acetyl, X=F, R$_{13}$=Ethyl, and D. M Taken Together=O;

The compound from step 12c is converted to the title compound following the procedure described in step 13a.

Step 14b. Compound of Formula I: A=—CH$_2$CH$_2$CH$_2$ CH$_2$CH$_2$-(4-(3-pyridyl)-1-imidazolyl), R$_1$=—CH$_2$CHCH$_2$, R$_p$=H, X=F, R$_{13}$=Ethyl, and D, M Taken Together=O.

The compound from step 14a is converted to the title compound following the procedure described in step 4e.

Example 15

Compound of Formula I: A=—CH$_2$CH$_2$CH$_2$-(3-quinolyl), R$_1$=H, R$_p$=H, R$_{13}$=Ethyl, and D, M
Taken Together=N—OH To a solution of compound from example 3 in ethanol is added hydroxylamine hydrochloride and imidazole. The reaction mixture is refluxed for 1–2 days and the solvent is removed under vacuum. The residue is taken up to ethyl acetate and washed with sodium bicarbonate, brine and water. The organic layer is dried over Na$_2$SO$_4$ and concentrated under vacuum. The residue is purified by chromatography on a silica gel column to give the title compound.

Example 16

Compound of Formula I: A=—CH$_2$CH$_2$CH$_2$-(3-quinolyl), R$_1$=H, R$_p$=H, R$_{13}$=Ethyl, and D, M
Taken Together=N—OCH$_2$OMe To a solution of compound from example 15 and TEA in THF is added MOMCl at 0° C. The mixture is stirred at room temperature for over night. Diluted with ethyl acetate and washed with sodium bicarbonate, brine and water. The organic layer is dried over Na$_2$SO$_4$ and concentrated under vacuum. The residue is purified by chromatography on a silica gel column to give the title compound.

Examples 17 through 26 may be prepared according to the procedures described in Examples 1 through 16 and the synthetic schemes and discussions contained herein.

Example 17

Compound of Formula I: A=—CH$_2$CH$_2$CH$_2$CH$_2$-(3-quinolyl), R$_1$=H, R$_p$=H, R$_{13}$=Ethyl, and D, M Taken Together=O

Example 18

Compound of Formula I: A=—CH$_2$CH$_2$CH$_2$CH$_2$-(4-quinolyl), R$_1$=H, R$_p$=H, R$_{13}$=Ethyl, and D, M Taken Together=O

Example 19

Compound of Formula I: A=—CH$_2$CH$_2$CH$_2$CH$_2$-(4-(3-pyridyl)-1H-pyrazolyl), R$_1$=H, R$_p$=H, R$_{13}$=Ethyl, and D, M Taken Together=O

Example 20

Compound of Formula I: A=—CH$_2$CH$_2$CH$_2$CH$_2$-(1-benzimidazolyl), R$_1$=H, R$_p$=H, R$_{13}$=Ethyl, and D, M Taken Together=O

Example 21

Compound of Formula I: A=—CH$_2$CH$_2$CH$_2$CH$_2$-(1-(4-azabenzimidazolyl), R$_1$=H, R$_{13}$=Ethyl, and D, M Taken Together=O

Example 22

Compound of Formula I: A=—CH$_2$CH$_2$CH$_2$CH$_2$-(3-quinolyl), R$_1$=H, R$_p$=H, X=F, R$_{13}$=Ethyl, and D, M Taken Together=O

Example 23

Compound of formula I: A=—CH$_2$CH$_2$CH$_2$CH$_2$-(4-quinolyl), R$_1$=H, R$_p$=H, X=F, R$_{13}$=Ethyl, and D, M Taken Together=O

Example 24

Compound of Formula I: A=—CH$_2$CH$_2$CH$_2$CH$_2$-(4-(3-Pyridyl)-1H-Pyrazolyl), R$_1$=H, R$_p$=H, X=F, R$_{13}$=Ethyl, and D, M Taken Together=O

Example 25

Compound of Formula I: A=—CH$_2$CH$_2$CH$_2$CH$_2$-(1-benzimidazolyl), R$_1$=H, R$_p$=H, X=F, R$_{13}$=Ethyl, and D, M Taken Together=O

Example 26

Compound of Formula I: A=—CH$_2$CH$_2$CH$_2$CH$_2$-(1-(4-azabenzimidazolyl), R$_1$=H, R$_p$=H, X=F, R$_{13}$=Ethyl and D, M Taken Together=O

What is claimed is:

1. A compound represented by formula (I):

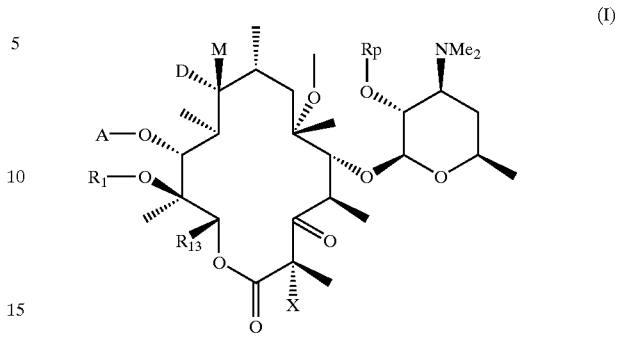

In formula (I) above,

A is selected from the group consisting of;
(1) C$_1$–C$_6$-alkyl, C$_2$–C$_6$-alkenyl or C$_2$–C$_6$-alkynyl, substituted with one or more substituents selected from the group consisting of:
   a. —O—R$_5$, where R$_5$ is selected from the group consisting of:
      i. aryl;
      ii. substituted aryl;
      iii. heteroaryl; and
      iv. substituted heteroaryl;
   b. —O—C$_1$—C$_6$alkyl, optionally substituted with R$_5$ where R$_5$ is as previously defined;
   c. —O—C$_1$–C$_6$-alkenyl, optionally substituted with R$_5$, where R$_5$ is as previously defined;
   d. —O—C$_2$–C$_6$-alkynyl, optionally substituted with R$_5$, where R$_5$ is as previously defined;
   e. —NR$_6$R$_7$, where R$_6$ and R$_7$ are each independently selected from C$_1$–C$_6$-alkyl, substituted with one or more substituents selected from the group consisting of halogen, aryl, substituted aryl, heterocyclic and substituted heterocyclic; C$_2$–C$_6$-alkenyl, optionally substituted with one or more substituents selected from the group consisting of halogen, aryl, substituted aryl, heterocyclic and substituted heterocyclic; C$_2$–C$_6$-alkynyl, optionally substituted with one or more substituents selected from the group consisting of halogen, aryl, substituted aryl, heterocyclic and substituted heterocyclic;
(3) —C(O)—R$_5$, where R$_5$ is as previously defined;
(4) —C(O)—C$_1$–C$_6$-alkyl, optionally substituted with R$_5$, where R$_5$ is as previously defined;
(5) —C(O)—C$_2$–C$_6$-alkenyl, optionally substituted with R$_5$, where R$_5$ is as previously defined;
(6) —C(O)—C$_2$–C$_6$-alkynyl, optionally substituted with R$_5$, where R$_5$ is as previously defined;
(7) —C$_1$–C$_6$-alkyl-M—R$_5$, where M—OC(O)—, —OC(O)O—, —OC(O)NR$_5$—, —NR$_6$C(O)—, —NR$_6$C(O)O—, —NR$_6$C(O)NR$_7$—, —NR$_6$C(N)NR$_7$—, S(O)$_n$—, where n=0, 1 or 2, and where R$_5$, R$_6$, R$_7$ are as previously defined;
(8) —C$_2$–C$_6$-alkenyl-M—R$_5$, where M—OC(O)—, —OC(O)O—, —OC(O)NR$_5$—, —NR$_6$C(O)—, —NR$_6$C(O)O—, —NR$_6$C(O)NR$_7$—, —NR$_6$C(N)NR$_7$—, S(O)$_n$—, where n=0, 1 or 2, and where R$_5$, R$_6$, R$_7$ are as previously defined; and
(9) —C$_2$–C$_6$-alkynyl-M—R$_5$, where M—OC(O)—, —OC(O)O—, —OC(O)NR$_6$—, —NR$_6$C(O)—, —NR$_6$C(O)O—, —NR$_6$C(O)NR$_7$—, —NR$_6$C(N)NR$_7$—, S(O)$_n$—, where n=0, 1 or 2, and where R$_5$, R$_6$, R$_7$ are as previously defined;

$R_1$ is selected from the group consisting of:
(1) hydrogen;
(2) $R_3$, where $R_3$ is $C_1$-$C_6$-alkyl, $C_2$-$C_6$-alkenyl or $C_2$-$C_6$-alkynyl, optionally substituted with one or more substituents selected from the group consisting of:
   a. halogen;
   b. aryl;
   c. substituted aryl;
   d. heteroaryl;
   e. substituted heteroaryl;
   f. —O—$C_1$—$C_6$alkyl—$R_5$, where $R_5$ is as previously defined; and
   g. —$NR_6R_7$, where $R_6$ and $R_7$, are as previously defined;
(3) —C(=O)—$R_4$, where $R_4$ is H or $R_3$ as previously defined;
(4) —C(=O)O—$R_3$, where $R_3$ is as previously defined; and
(5) —C(=O)N—$R_6R_7$, where $R_6$ and $R_7$ are as previously defined;

D and M are selected from the group consisting of:
(1) one of D and M is hydrogen and the other is selected from the group consisting of:
   i. hydrogen;
   ii. hydroxy;
   iii. protected hydroxy; and
   iv. —$NR_6R_7$, where $R_6$ and $R_7$ are as previously defined; and
(2) D and M taken together define Y, where Y is selected from the group consisting of:
   a. =O;
   b. =N—OH;
   c. =N—O—$R_8$, where $R_8$ is a $C_1$-$C_6$-alkyl group, optionally substituted with a group selected from an aryl, substituted aryl, heteroaryl, or substituted heteroaryl; and
   d. =N—O—C($R_9$)($R_{10}$)—O—$R_{11}$, where $R_9$ and $R_{10}$ are each independently selected from the group consisting of hydrogen or $C_1$-$C_6$-alkyl, and $R_{11}$ is selected from the group consisting of:
      i. $R_8$, as previously defined;
      ii. —$C_1$-$C_6$-alkyl, optionally substituted with $C_1$-$C_6$-alkoxy and
      iii. —$C_1$-$C_6$-alkyl—O—$C_1$-$C_6$-alkyl—$R_5$, where $R_5$ is as previously defined;

X is selected from the group consisting of:
(1) hydrogen;
(2) methyl; and
(3) halogen;

$R_{13}$ is selected from:
(1) hydrogen,
(2) $C_1$-$C_6$-alkyl optionally substituted with halogen,
(3) $C_2$-$C_6$-alkenyl,
(4) $C_2$-$C_6$-alkynyl, or
(5) —$CH_2$—R″, where R″ is selected from hydrogen, $C_1$-$C_6$-alkyl, $C_2$-$C_6$-alkenyl, $C_2$-$C_6$-alkynyl or phenyl, optionally substituted with halogen, or $C_1$-$C_6$-alkyl optionally substituted with $R_5$, where $R_5$ is as defined previously;
(6) —$C_3$-$C_8$-cycloalkyl; and Rp is hydrogen or hydroxy protecting group.

2. The compound according to claim 1, where $R_{13}$=—$CH_2CH_3$.

3. The compound according to claim 2, where D and M taken together=O.

4. A compound as defined in claim 1 which is selected from the group consisting of:

Compound of formula I: A=—$CH_2CH_2CH_2CH_2$-(4-(3-pyridyl)-1-imidazolyl), $R_1$=C(O)$NH_2$, $R_p$=H, X=H, $R_{13}$=ethyl, and D, M taken together=O;

Compound of formula I: A=—$CH_2CH_2CH_2CH_2$-(4-phenyl)-1-imidazolyl), $R_1$=$CH_2CHCH_2$, $R_p$=H, X=H, $R_{13}$=ethyl, and D, M taken together=O;

Compound of formula I: A=—$CH_2CH_2CH_2CH_2$-(4-(3-pyridyl)-1-imidazolyl), $R_1$=$CH_2CHCH_2$, $R_p$=H, X=H, $R_{13}$=ethyl, and D, M taken together=O;

Compound of formula I: A=—$CH_2CH_2CH_2CH_2CH_2$-(4-phenyl)-1-imidazolyl), $R_1$=$CH_2CHCH_2$, $R_p$=H, X=H, $R_{13}$=ethyl, and D, M taken together=O;

Compound of formula I: A=—$CH_2CH_2CH_2CH_2CH_2$-(4-(3-pyridyl)-1-imidazolyl), $R_1$=$CH_2CHCH_2$, $R_p$=H, X=H, $R_{13}$=ethyl, and D, M taken together=O;

Compound of formula I: A=—$CH_2CH_2CH_2CH_2$-(4-(3-pyridyl)-1-imidazolyl), $R_1$=$CH_2CHCH_2$, $R_p$=H, X=H, $R_{13}$=ethyl, and D, M taken together=O; and Compound of formula I: A=—$CH_2CH_2CH_2CH_2CH_2$-(4-(3-pyridyl)-1-imidazolyl), $R_1$=$CH_2CHCH_2$, $R_p$=H, X=H, $R_{13}$=ethyl, and D, M taken together=O.

5. A pharmaceutical composition for treating bacterial infections comprising a therapeutically effective amount of a compound of claims 1 or 2 or a pharmaceutically acceptable salt, ester or prodrug thereof in combination with a pharmaceutically acceptable carrier.

6. A method for treating bacterial infections comprising administering to a mammal in need of such treatment a pharmaceutical composition containing a therapeutically-effective amount of a compound of claims 1 or 2 or a pharmaceutically acceptable salt, ester or prodrug thereof.

7. A process for the preparation of a compound represented by formula I, as in claim 1 comprising the steps:

(a) reacting a compound represented by the formula:

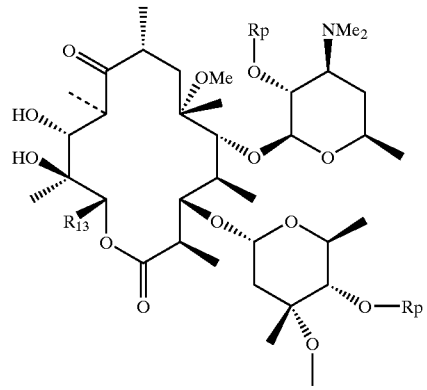

where Rp and $R_{13}$ are as defined in claim 1, with a tert-butyl allyl carbonate and a palladium catalyst with a phosphorus ligand in an aprotic solvent to provide a compound represented by the formula:

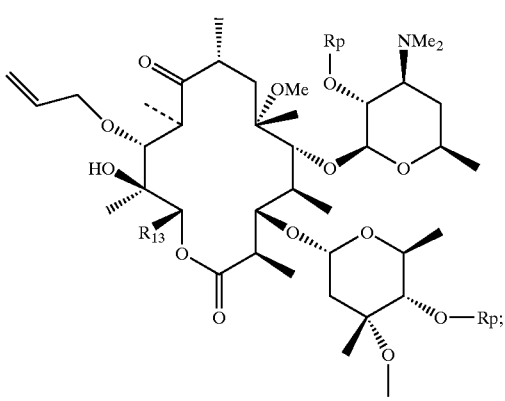

(b) reacting the product of step (a) with an aryl halide or an aryl triflate, where the said aryl group is an R group selected from an aryl, heteroaryl, substituted aryl, or substituted heteroaryl group, in the presence of a palladium catalyst with a phosphorus ligand to provide a compound represented by the formula:

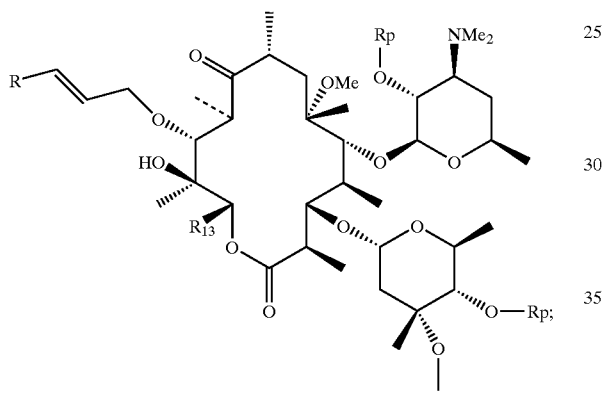

(c) the product of step (b) is optionally first hydrogenated, with palladium on carbon under hydrogen at a temperature between 0° C. 50° C. directly subjected to acid hydrolysis at a temperature between 0° C. to 70° C. to provide a compound represented by the formula:

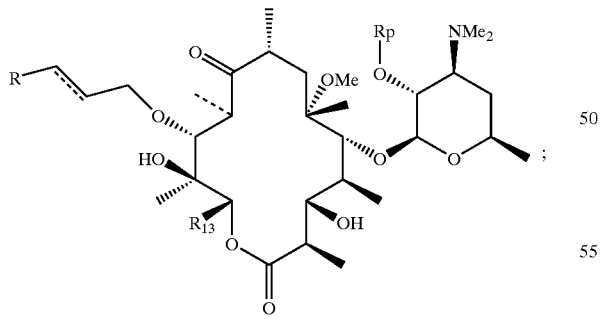

(d) the product of step (c) is treated with an oxidizing agent in an aprotic solvent at at a temperature between 0° C. to 50° C. and treated with methanol from 0° C. to 60° C. to provide a compound represented by formula I in claim 1, where A=—$CH_2CH=CHR$ or —$CH_2CH_2CH_2R$, D and M taken together=O, $R_{13}$ is as defined in claim 1, and X, $R_1$ and Rp are H.

8. A process for the preparation of a compound represented by formula I, as in claim 1 comprising the steps:

(a) reacting a compound represented by the formula:

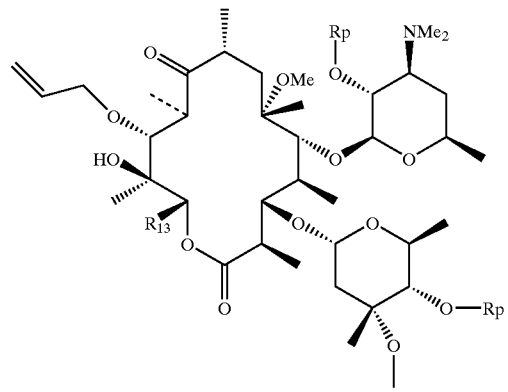

where Rp and $R_{13}$ are as defined in claim 1, with an aryl-alkenyl derivative of the formula R—$(CH_2)_n$—CH=$CH_2$, where n=1, 2 or 3, using ruthenium catalysts, where the said R group is selected from an aryl, heteroaryl, substituted aryl, or substituted heteroaryl group, at a temperature between 0° C. to 50° C. in an aprotic solvent to provide a compound represented by the formula:

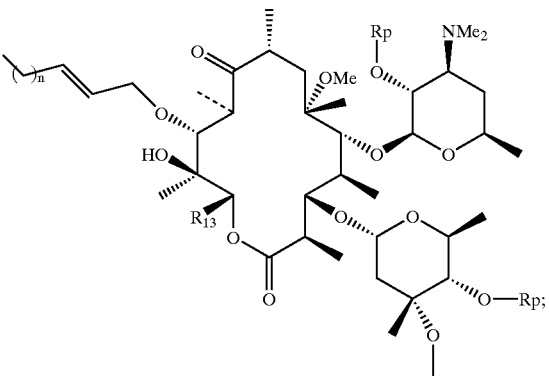

(b) the product of step (a) is optionally first hydrogenated, with palladium on carbon under hydrogen at a temperature between 0° C. to 50° C., or directly subjected to acid hydrolysis at a temperature between 0° C. to 70° C. to provide a compound represented by the formula:

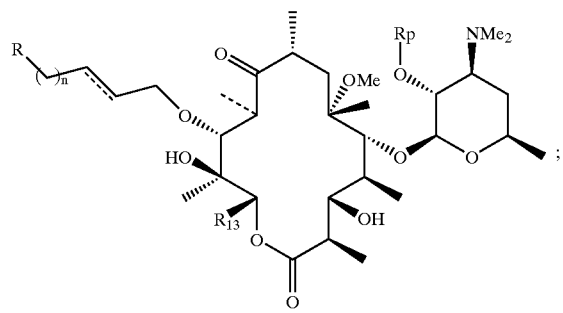

(c) the product of step (b) is treated with an oxidizing agent in an aprotic solvent at at a temperature between 0° C. to 50° C. and treated with methanol from 0° C. to 60° C. to provide a compound represented by formula I in claim 1, where A=—$CH_2CH=CH(CH_2)_nR$ or —CH$_2$CH$_2$CH$_2$(CH$_2$)$_n$R where n=1, 2 or 3, D and M taken together=O, R$_{13}$ is as defined in claim 1, and X, R$_1$, and Rp are H.

9. A process for the preparation of a compound represented by formula I, as in claim 1 comprising the steps:

(a) a compound represented by the formula:

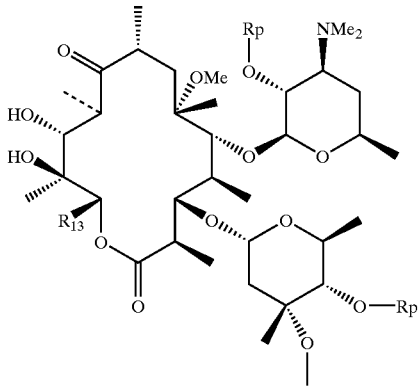

where Rp and R$_{13}$ are as defined in claim 1, is subjected to acid hydrolysis at a temperature between 0° C. to 70° C. and treated with an oxidizing agent in an aprotic solvent at a temperature between 0° C. to 50° C. to provide a compound represented by the formula:

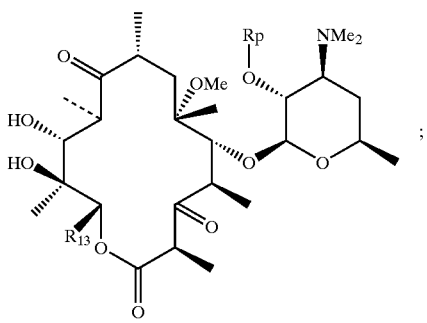

(b) reacting the product of step (a) with a tert-butyl allyl carbonate catalyzed by a palladium catalyst with a phosphorus ligand in an aprotic solvent to provide a compound represented by the formula:

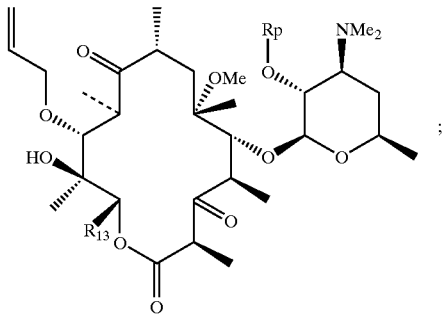

(c) the product of step (b) is:

i. teacted with an aryl halide or an aryl triflate, where the said aryl group is an R group selected front an aryl, heteroaryl, substituted aryl, or substituted heteroaryl group, in the presence of a palladium catalyst with a phosphorus ligand, optionally hydrogenated with palladium on carbon under hydrogen at a temperature between 0° C. to 50° C.; and ii. treated with methanol from 0° to 60° to provide a compound represented by formula I in claim 1, where A=—CH$_2$CH═CH(CH$_2$)$_n$R or —CH$_2$CH$_2$CH$_2$(CH$_2$)$_n$R where n=1,2 or 3, and M taken together=O, R$_{13}$ is as defined in claim 1, and X, R$_1$ and Rp are H.

10. A process forte preparation of a compound represented by formula I, as in claim 1 comprising the steps:

(a) reacting a compound represented by the formula:

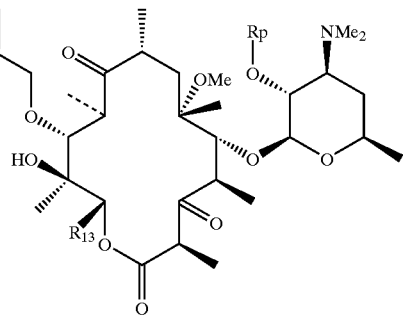

where Rp is as defined in claim 1, with an aryl-alkenyl derivative of the formula R—(CH$_2$)$_n$—CH═CH$_2$, where n=1, 2 or 3, using ruthenium catalysts, where the said R group is selected from an aryl, heteroaryl, substituted aryl, or substituted heteroaryl group, at a temperature between 0° to 50° in an aprotic solvent to provide a compound represented by the formula:

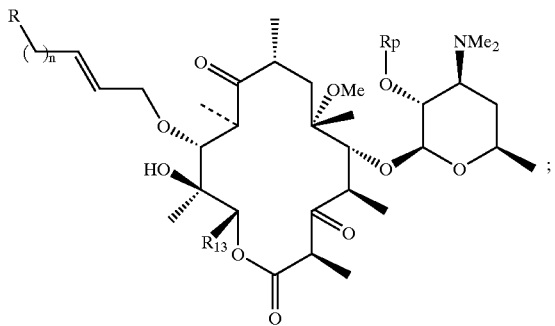

(b) the product of step (a) is optionally first hydrogenated, with palladium on carbon under hydrogen at a temperature between 0° to 50° C., and treated with methanol from 0° to 60° to provide a compound represented by formula I in claim 1, where A=CH$_2$CH═CH(CH$_2$)$_n$R or —CH$_2$CH$_2$CH$_2$(CH$_2$)$_n$R where n=1, 2 or 3, D and M taken together=O, R$_{13}$ is as defined in claim 1, and X, R$_1$ and Rp are H.

11. A process for the preparation of a compound represented by formula I, as in claim 1 comprising the steps:

(a) reacting a compound represented by the formula:

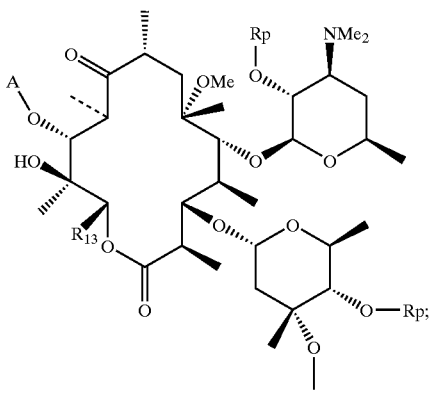

where A, Rp and $R_{13}$ are as defined in claim 1, with a tert-butyl allyl carbonate catalyzed by a palladium catalyst with a phosphorus ligand in an aprotic solvent for 30 to 40 hours at a temperature between 40° C. and 80° C. to provide a compound represented by the formula:

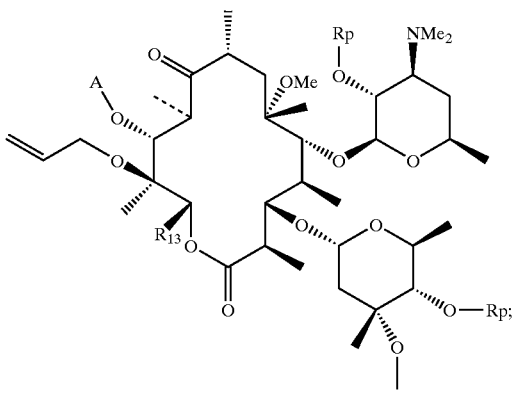

(b) the product of step (a) is subjected to acid hydrolysis at a temperature between 0° C. to 70° C. and created with an oxidizing agent in an aprotic solvent at a temperature between 0° C. to 50° C. to provide a compound represented by the formula:

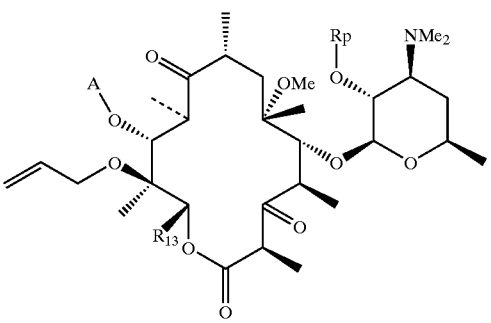

(c) the product of step (b) is treated with methanol from 0° C. to 60° C. to provide a compound represented by formula I in claim 1, where A and $R_{13}$ are as defined in claim 1, D and M taken together=O, X and Rp are H, and $R_1$=—$CH_2CH=CH_2$.

\* \* \* \* \*